US008093046B2

(12) United States Patent
McFadden et al.

(10) Patent No.: US 8,093,046 B2
(45) Date of Patent: Jan. 10, 2012

(54) CVN-12P1: A RECOMBINANT ALLOSTERIC LECTIN ANTAGONIST OF HIV-1 ENVELOPE GP120 INTERACTIONS

(75) Inventors: Karyn McFadden, Philadelphia, PA (US); Irwin M. Chaiken, Gladwyne, PA (US)

(73) Assignee: Philadelphia Health and Education Corporation d/b/c Drexel University College of Medicine, Philadelphia, PA (US)

( * ) Notice: Subject to any disclaimer, the term of this patent is extended or adjusted under 35 U.S.C. 154(b) by 909 days.

(21) Appl. No.: 11/756,567

(22) Filed: May 31, 2007

(65) Prior Publication Data

US 2009/0233850 A1     Sep. 17, 2009

Related U.S. Application Data

(60) Provisional application No. 60/803,564, filed on May 31, 2006.

(51) Int. Cl.
    C12N 5/02      (2006.01)
    C07K 7/00      (2006.01)
    G01N 33/53     (2006.01)
    A61K 39/00     (2006.01)
(52) U.S. Cl. ............... 435/375; 530/327; 424/184.1; 424/187.1; 424/188.1; 424/185.1; 424/194.1
(58) Field of Classification Search .................. None
    See application file for complete search history.

(56) References Cited

U.S. PATENT DOCUMENTS

| 5,821,081 | A | * | 10/1998 | Boyd et al. ............... 435/69.1 |
| 5,843,882 | A |   | 12/1998 | Boyd |
| 6,015,876 | A |   | 1/2000  | Boyd |
| 6,586,392 | B2 |   | 7/2003  | Boyd |
| 6,743,577 | B2 |   | 6/2004  | Boyd |

FOREIGN PATENT DOCUMENTS

| WO | WO 95/26199   | * | 3/1995  |
| WO | WO2004/067030 | * | 1/2004  |
| WO | WO 2008/150444|   | 12/2008 |

OTHER PUBLICATIONS

Tsai C-C et al. "Cyanovirin-N Gel as a Topical Microbicide Prevents Rectal Transmission of SHIV89.6P in Macaques" AIDS Research and Human Retroviruses vol. 19, No. 7, 2003, pp. 535-541.*
Chou TC, Talalay P. Applications of the median effect principle for the assessment of low dose risk of carcinogens and for the quantitation of synergism and antagonism of chemotherapeutic agents. In: Harrap KR, Conners TA, editors. New avenues in developmental cancer chemotherap. New York: Academic Press; 1987. p. 37-63.
Culp JS, Johansen H, Hellmig B, Beck J, Matthews TJ, Delers A, Rosenberg M. Regulated expression allows high level production and secretion of HIV-1 gp120 envelope glycoprotein in Drosophila Schneider cells. Biotechnology (NY) 1991;9(2):173-177.
Chou TC. The Median-Effect Principle and the Combination Index for Quantitation of Synergism and Antagonism. In: Rideout DC, editor. Synergism and Antagonism in Chemotherapy. San Diego: San Diego Academic Press; 1991. p. 61.
Posner MR, Cavacini LA, Emes CL, Power J, Byrn R. Neutralization of HIV-1 by F105, a human monoclonal antibody to the CD4 binding site of gp120. J Acquir Immune Defic Syndr 1993;6(1):7-14.
Posner MR, Elboim HS, Cannon T, Cavacini L, Hideshima T. Functional activity of an HIV-1 neutralizing IgG human monoclonal antibody: ADCC and complement-mediated lysis. AIDS Res Hum Retroviruses 1992;8(5):553-558.
Biorn et al., "Mode of Action for Linear Peptide Inhibitors of HIV-2 gp120 Interactions," Biochemistry 2004 43:1928-1938.
Boyd et al., 1997, "Discovery of Cyanovirin-N, a Novel Human Immunodeficiency Virus-Inactivating Protein That Binds Viral Surface Envelope Glycoportine gp120: Potential Applications to Microbicide Development," Antimicrob Agents Chemother. 41(7):1521-1530.
Chan et al., "Core Structure of gp41 from the HIV Envelope Glycoprotein," Cell 1997 89:263-273.
Dalgleish et al., "The CD4 (T4) antigen is an essential component of the receptor for the AIDS retrovirus," Nature 1984 312 (20/27) : 763-767.
Dey et al., 2000, "Multiple antiviral activities of cyanovirin-N: blocking of human immunodeficiency virus type 1 gp120 interaction with CD4 and coreceptor and inhibition of diverse enveloped viruses.," J. Virol. 74:4562-4569.
Dragic et al., "HIV-1 entry into CD4+ cells is mediated by the chemokine receptor CC-CKR-5," Nature 1996 381:667-673.
Esser et al., 1999, "Cyanovirin-N binds to gp120 to interfere with CD4-dependent human immunodeficiency virus type 1 virion binding, fusion, and infectivity but does not affect the CD4 binding site on gp120 or soluble CD4-induced conformational changes in gp120," J Virol. 73(5):4360-4371.
Feng et al., "HIV-1 Entry Cofactor:Functional cDNA Cloning of a Seven-Transmembrane, G Protein-Coupled Receptor," Science 1996 272:872-877.
Ferrer et al., "Peptide Ligands to Human Immunodeficiency Virus Type 1 gp120 Identified from Phage Display Libraries," Journal of Virology 1999 73(7):5795-5802.
Klatzmann et al., "T-lymphocyte T4 molecule behaves as the receptor for human retrovirus LAV," Nature 1984 312 (20/27) : 767-768.
Tan et al., "Atomic structure of a thermostable subdomain of HIV-1 gp411," Proc. Natl. Acad. Sci. USA 1997 94:12303-12308.
Trkola et al., "CD4-dependent, antibody-sensitive interactions between HIV-1 and its co-receptor CCR-5," Nature 1996 384:184-187.
Tsai et al., 2004, "Cyanovirin-N inhibits AIDS virus infections in vaginal transmission models," AIDS Res Hum Retroviruses. 20(1):11-8.

(Continued)

Primary Examiner — Bo Peng
(74) Attorney, Agent, or Firm — Riverside Law LLP

(57) ABSTRACT

The invention provides a recombinant multi-functional chimera of CVN and 12p1. Chimeras of CVN and 12p1 present a model for targeting gp120 at two discrete sites, by two different modes of inhibition and with increasing potency versus either component alone. A chimera of the invention combines the high affinity suppression of viral activity by CVN with the allosteric suppression of viral envelope binding to both CD4 and co-receptor by 12p1.

11 Claims, 12 Drawing Sheets

OTHER PUBLICATIONS

Wu et al., "CD4-induced interaction of primary HIV-1 gp120 glycoproteins with the chemokine receptor CCR-5," *Nature* 1996 384:179-183.

Wyatt et al., "The HIV-1 Envelope Glycoproteins:Fusogens, Antigens, and Immunogens," *Science* 1998 280:1884-1888.

Zappe et al., 2008, "PEGylation of cyanovirin-N, an entry inhibitor of HIV," Adv Drug Deliv Rev. 60:79-87; E-published Aug. 16, 2007; Abstract only.

Abuchowski, et al., "Alteration of immunological properties of bovine serum albumin by covalent attachment of polyethylene glycol," *J Biol Chem.*, Jun. 1977, 252(11):3578-3581.

Abuchowski, et al., "Soluble Polymer-Enzyme Adducts" in *Enzymes as Drugs*, Holcenberg et al., eds., John Wiley: New York, 1981, pp. 367-378.

Barry, "The Transdermal Route for the Delivery of Peptides and Proteins" in *Delivery Systems for Peptide Drugs*, Davis et al., eds., Plenum Press: New York, 1986, pp. 265-275.

Bewley, "Solution Structure of a Cyanovirin-N:Manα1-2Manα Complex: Structural Basis for High-Affinity Carbohydrate-mediated Binding to gp120", *Structure*, vol. 9, 931-940, Oct. 2001.

Bird, "The use of spermicide containing nonoxynol-9 in the prevention of HIV infection," *AIDS*, Jul. 1991, 5(7):791-796.

Bourinbalar, et al., "Anti-HIV Effect of Gramicidin In Vitro: Potential for Spermicide Use," *Life Sci.* 1994, 54(1):PL5-9.

Bourinbalar, et al., "Comparative in vitro study of contraceptive agents with anti-HIV activity: Gramicidin, nonoxynol-9, and gossypol," *Contraception*, 1994, 49:131-137.

Cocklin, et al., "Broad-spectrum anti-human immunodeficiency virus (HIV) potential of a peptide HIV type 1 entry inhibitor," *J. Virol.*, Apr. 2007, 81(7):3645-3648. EPUB Jan. 24, 2007.

Davis, "Delivery Systems for Biopharmaceuticals," *J. Pharm Pharmacol.*, Feb. 1992, 44 Suppl 1:186-190.

Deasy, (1984), *Microencapsulation and Related Processes*, Marcell Dekker, Inc.: New York, Chapters 1 and 2, pp. 1-60.

Deasy, (1984), *Microencapsulation and Related Processes*, Marcell Dekker, Inc.: New York, Chapter 3 excerpt, pp. 88-89.

Deasy, (1984), *Microencapsulation and Related Processes*, Marcell Dekker, Inc.: New York, Chapter 9 excerpt, pp. 208-211.

Kashman et al., "The calanolides, a novel HIV-inhibitory class of coumarin derivatives from the tropical rainforest tree, *Calophyllum lanigerum*," *J Med Chem.*, Jul. 1992, 35(15):2735-2743.

Lin, et al., "Selective inhibition of human immunodeficiency virus type 1 replication by the (−) but not the (+) enantiomers of gossypol," *Antimicrob Agents Chemother,* Dec. 1989, 33(12):2149-2151.

Maulding, "Prolonged delivery of peptides in microcapsules," Original Research Article *Journal of Controlled Release,* vol. 6, Issue 1, Dec. 1987, pp. 167-176.

Merigan, "Treatment of AIDS with combinations of antiretroviral agents," *Am J Med.* Apr. 1991, 90(4A):8S-17S.

Nicholl, (1994) *An Introduction to Genetic Engineering,* Cambridge University Press: Cambridge, Chapter 1, pp. 1-7.

Nicholl, (1994) *An Introduction to Genetic Engineering,* Cambridge University Press: Cambridge, Chapter 7 excerpt, pp. 127-130.

Patton, et al., "(D) Routes of Delivery: Case Studies: (2) Pulmonary delivery of peptides and proteins for systemic action," Review Article *Advanced Drug Delivery Reviews*, vol. 8, Issues 2-3, Mar.-Jun. 1992, pp. 179-196.

Polsky, et al., "Inactivation of human immunodeficiency virus in vitro by gossypol," *Contraception,* Jun. 1989, 39(6):579-587.

Royer, et al., "Inhibition of human immunodeficiency virus type 1 replication by derivatives of gossypol," *Pharmacol Res.,* Dec. 1991, 24(4):407-412.

Shih, et al., "Chimeric human immunodeficiency virus type 1/type 2 reverse transcriptases display reversed sensitivity to nonnucleoside analog inhibitors," *Proc Natl Acad Sci USA,* Nov. 1991, 88(21):9878-9882.

van Hoogdalem, et al., "Intestinal Drug Absorption Enhancement: An overview," *Pharmacol Ther.,* 1989, 44(3):407-443.

Verhoef, et al., "Transport of peptide and protein drugs across biological membranes," *Eur J Drug Metab Pharmacokinet.,* Apr.-Jun. 1990 15(2):83-93.

Wallace, et al., "Stand and deliver: Getting peptide drugs into the body," *Science,* May 1993, 260(5110):912-915.

Wileman et al., "Soluble asparaginase-dextran conjugates show increased circulatory persistance and lowered antigen reactivity," J. Pharm. Pharmacol., 1986, 38:264-271.

Yang et al., "Crystal Structure of Cyanovirin-N, a Potent HIV-inactivating Protein, Shows Unexpected Domain Swapping", *J. Mol. Biol.* 1999, 288:403-412.

\* cited by examiner

FIG. 2B

| | | | |
|---|---|---|---|
| CV-N | CVN | His — C | |
| L5 | CVN | (Gly₄Ser)₅ | His — C |
| L5-S12p1 | CVN | (Gly₄Ser)₅ | WRIMMIPSEANN | His — C |

(Note: L5 contains RINNIPWSEAMM; L5-S12p1 contains WRIMMIPSEANN)

SEQUENCE LISTING

```
<160> NUMBER OF SEQ ID NOS: 15

<210> SEQ ID NO 1
<211> LENGTH: 327
<212> TYPE: DNA
<213> ORGANISM: Artificial Sequence
<220> FEATURE:
<223> OTHER INFORMATION: Chemically Synthesized

<400> SEQUENCE: 1
cgatcgaagc ttggtaaatt ctcccagacc tgctacaact ccgctatcca gggttccgtt      60
ctgacctcca cctgcgaacg taccaacggt ggttacaaca cctcctccat cgacctgaac     120
tccgttatcg aaaacgttga cggttccctg aaatggcagc cgtccaactt catcgaaacc     180
tgccgtaaca cccagctggc tggttcctcc gaactggctg ctgaatgcaa aacccgtgct     240
cagcagttcg tttccaccaa aatcaacctg gacgaccaca tcgctaacat cgacggtacc     300
ctgaaatacg aataactcga gatcgta                                         327

<210> SEQ ID NO 2
<211> LENGTH: 101
<212> TYPE: PRT
<213> ORGANISM: Artificial Sequence
<220> FEATURE:
<223> OTHER INFORMATION: Chemically Synthesized

<400> SEQUENCE: 2

Leu Gly Lys Phe Ser Gln Thr Cys Tyr Asn Ser Ala Ile Gln Gly Ser
```

```
                1               5              10              15
Val Leu Thr Ser Thr Cys Glu Arg Thr Asn Gly Gly Tyr Asn Thr Ser
                       20                  25                  30

Ser Ile Asp Leu Asn Ser Val Ile Glu Asn Val Asp Gly Ser Leu Lys
                35                  40                  45

Trp Gln Pro Ser Asn Phe Ile Glu Thr Cys Arg Asn Thr Gln Leu Ala
            50                  55                  60

Gly Ser Ser Glu Leu Ala Ala Glu Cys Lys Thr Arg Ala Gln Gln Phe
 65                 70                  75                  80

Val Ser Thr Lys Ile Asn Leu Asp Asp His Ile Ala Asn Ile Asp Gly
                    85                  90                  95

Thr Leu Lys Tyr Glu
                100
```

<210> SEQ ID NO 3
<211> LENGTH: 327
<212> TYPE: DNA
<213> ORGANISM: Artificial Sequence
<220> FEATURE:
<223> OTHER INFORMATION: Chemically Synthesized

<400> SEQUENCE: 3

```
gactacaagg acgacgatga caagcttggt aaattctccc agacctgcta caactccgct      60
atccagggtt ccgttctgac ctccacctgc gaacgtacca acggtggtta caacacctcc     120
tccatcgacc tgaactccgt tatcgaaaac gttgacggtt ccctgaaatg gcagccgtcc     180
aacttcatcg aaacctgccg taacacccag ctggctggtt cctccgaact ggctgctgaa     240
tgcaaaaccc gtgctcagca gttcgtttcc accaaaatca acctggacga ccacatcgct     300
aacatcgacg gtaccctgaa atacgaa                                         327
```

<210> SEQ ID NO 4
<211> LENGTH: 109
<212> TYPE: PRT
<213> ORGANISM: Artificial Sequence
<220> FEATURE:
<223> OTHER INFORMATION: Chemically Synthesized

<400> SEQUENCE: 4

```
Asp Tyr Lys Asp Asp Asp Lys Leu Gly Lys Phe Ser Gln Thr Cys
 1               5              10              15

Tyr Asn Ser Ala Ile Gln Gly Ser Val Leu Thr Ser Thr Cys Glu Arg
                20                  25                  30

Thr Asn Gly Gly Tyr Asn Thr Ser Ser Ile Asp Leu Asn Ser Val Ile
                35                  40                  45

Glu Asn Val Asp Gly Ser Leu Lys Trp Gln Pro Ser Asn Phe Ile Glu
            50                  55                  60

Thr Cys Arg Asn Thr Gln Leu Ala Gly Ser Ser Glu Leu Ala Ala Glu
 65                 70                  75                  80

Cys Lys Thr Arg Ala Gln Gln Phe Val Ser Thr Lys Ile Asn Leu Asp
                    85                  90                  95

Asp His Ile Ala Asn Ile Asp Gly Thr Leu Lys Tyr Glu
                100                 105
```

<210> SEQ ID NO 5
<211> LENGTH: 303
<212> TYPE: DNA
<213> ORGANISM: Artificial Sequence
<220> FEATURE:
<223> OTHER INFORMATION: Chemically Synthesized

<400> SEQUENCE: 5

```
cttggtaaat tctcccagac ctgctacaac tccgctatcc agggttccgt tctgacctcc      60
acctgcgaac gtaccaacgg tggttacaac acctcctcca tcgacctgaa ctccgttatc     120
gaaaacgttg acggttccct gaaatggcag ccgtccaact tcatcgaaac ctgccgtaac     180
acccagctgg ctggttcctc cgaactggct gctgaatgca aacccgtgc tcagcagttc      240
gtttccacca aaatcaacct ggacgaccac atcgctaaca tcgacggtac cctgaaatac     300
gaa                                                                    303
```

<210> SEQ ID NO 6
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 6

```
cggattaaca atatcccgtg gtcggaggcg atgatg                                36
```

<210> SEQ ID NO 7
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 7

```
attaacaata tcccgtggtc g                                                21
```

<210> SEQ ID NO 8
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 8

```
ggtggcggag ggtc                                                        14
```

<210> SEQ ID NO 9
<211> LENGTH: 81
<212> TYPE: DNA
<213> ORGANISM: Artificial Sequence
<220> FEATURE:
<223> OTHER INFORMATION: Chemically Synthesized

<400> SEQUENCE: 9

```
ggatccggtg gcggagggtc gggcggaggt ggaagcggag gtggcggtag tggtggaggc      60
ggatccggtg gcggagggtc t                                                81
```

<210> SEQ ID NO 10
<211> LENGTH: 420
<212> TYPE: DNA
<213> ORGANISM: Artificial Sequence
<220> FEATURE:
<223> OTHER INFORMATION: Chemically Synthesized

<400> SEQUENCE: 10

```
cttggtaaat tctcccagac ctgctacaac tccgctatcc agggttccgt tctgacctcc      60
acctgcgaac gtaccaacgg tggttacaac acctcctcca tcgacctgaa ctccgttatc     120
gaaaacgttg acggttccct gaaatggcag ccgtccaact tcatcgaaac ctgccgtaac     180
```

```
acccagctgg ctggttcctc cgaactggct gctgaatgca aaacccgtgc tcagcagttc    240
gtttccacca aaatcaacct ggacgaccac atcgctaaca tcgacggtac cctgaaatac    300
gaaggatccg gtggcggagg gtcgggcgga ggtggaagcg gaggtggcgg tagtggtgga    360
ggcggatccg gtggcggagg gtctcggatt aacaatatcc cgtggtcgga ggcgatgatg    420
```

<210> SEQ ID NO 11
<211> LENGTH: 438
<212> TYPE: DNA
<213> ORGANISM: Artificial Sequence
<220> FEATURE:
<223> OTHER INFORMATION: Chemically Synthesized

<400> SEQUENCE: 11

```
cttggtaaat tctcccagac ctgctacaac tccgctatcc agggttccgt tctgacctcc     60
acctgcgaac gtaccaacgg tggttacaac acctcctcca tcgacctgaa ctccgttatc    120
gaaaacgttg acggttccct gaatggcagc cgtccaact tcatcgaaac ctgccgtaac     180
acccagctgg ctggttcctc cgaactggct gctgaatgca aaacccgtgc tcagcagttc    240
gtttccacca aaatcaacct ggacgaccac atcgctaaca tcgacggtac cctgaaatac    300
gaaggatccg gtggcggagg gtcgggcgga ggtggaagcg gaggtggcgg tagtggtgga    360
ggcggatccg gtggcggagg gtctcggatt aacaatatcc cgtggtcgga ggcgatgatg    420
catcatcatc atcattaa                                                  438
```

<210> SEQ ID NO 12
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 12

Arg Ile Asn Asn Ile Pro Trp Ser Glu Ala Met Met
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 13

Ile Asn Asn Ile Pro Trp Ser
1               5

<210> SEQ ID NO 14
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 14

Trp Arg Ile Met Met Ile Pro Ser Glu Ala Asn Asn
1               5                   10

<210> SEQ ID NO 15
<211> LENGTH: 441
<212> TYPE: DNA
<213> ORGANISM: Artificial
<220> FEATURE:

<223> OTHER INFORMATION: Chemically synthesized
<220> FEATURE:
<221> NAME/KEY: misc_feature
<222> LOCATION: (1)..(441)
<223> OTHER INFORMATION: encodes L5 chimera with 6His tail

<400> SEQUENCE: 15

```
cttggtaaat tctcccagac ctgctacaac tccgctatcc agggttccgt tctgacctcc      60
acctgcgaac gtaccaacgg tggttacaac acctcctcca tcgacctgaa ctccgttatc     120
gaaaacgttg acggttccct gaaatggcag ccgtccaact tcatcgaaac ctgccgtaac     180
acccagctgg ctggttcctc cgaactggct gctgaatgca aaacccgtgc tcagcagttc     240
gtttccacca aaatcaacct ggacgaccac atcgctaaca tcgacggtac cctgaaatac     300
gaaggatccg gtggcggagg gtcgggcgga ggtggaagcg gaggtggcgg tagtggtgga     360
ggcggatccg gtggcggagg gtctcggatt aacaatatcc cgtggtcgga ggcgatgatg     420
catcatcatc atcatcatta a                                              441
```

CVN-12P1: A RECOMBINANT ALLOSTERIC LECTIN ANTAGONIST OF HIV-1 ENVELOPE GP120 INTERACTIONS

CROSS-REFERENCE TO RELATED APPLICATIONS

This application claims the benefit pursuant to 35 U.S.C. §119(e) of U.S. Provisional Application No. 60/803,564, filed on May 31, 2006.

STATEMENT REGARDING FEDERALLY SPONSORED RESEARCH OR DEVELOPMENT

This invention was made with government support under grant numbers P01 GM 56550 and PA-01-075 from the National Institutes of Health. The government has certain rights in the invention.

BACKGROUND OF THE INVENTION

1. Field of Invention

This invention relates to a retrovirus inhibitor and more specifically to an HIV inhibitor.

2. Description of Related Art

There were an estimated 40.3 million people infected with HIV in 2005, with close to 5 million people becoming newly infected. AIDS is affecting an increasing number of women worldwide particularly in developing countries where transmission occurs primarily through heterosexual intercourse. A discrete, female-controlled method of preventing HIV infection is of paramount importance in the battle against AIDS. Since an effective vaccine is still years from development, topical microbicides have gained increased attention. Topical microbicides are vaginally or rectally applied compounds designed to inactivate HIV and prevent infection that should ideally be effective, safe, inexpensive and easy to administer. Microbicides, compounds that could be used in vaginal and rectal formulations, are increasingly seen as an urgent goal to stop transmission.

Advances in our understanding of the mechanism of HIV entry and infection have led to the development of microbicides that can target HIV without harming the body's natural defense system (ref 1-4). The initial, critical step of HIV infection is its entry through the fusion of the viral membrane with the membrane of either a T-cell or macrophage. The fusion process is mediated by the viral envelope glycoprotein, gp120, and can be triggered by interaction of gp120 with the T-cell antigen receptor CD4 glycoprotein (ref 5-7). CD4 induces conformational changes in gp120 that are postulated to promote subsequent steps in the fusion process, such as co-receptor binding and dissociation of gp120 from p41 (ref. 8-9). Several seven-transmembrane chemokine receptors, mainly CCR5 and CXR4, have been identified as obligate co-receptors for viral entry into the host cell (ref 9-13). Blocking the binding of CD4 with gp120 or preventing the CD4-induced conformational isomerization that promotes co-receptor binding and viral cell fusion could have potential value for the prevention and treatment of HIV infection and AIDS.

One candidate for a topical microbicide targeting gp120 is cyanovirin-N(CVN), an 11 kD protein originally isolated from the cyanobacteria *Nostoc ellipsosporum* (ref 14). It inactivates a broad range of clades of HIV-1, SIV, and FIV, and prevents cell to cell transmission of infection. Recent investigations using both in vitro and in vivo assays yield support for the efficacy of CV-N as a microbicidal candidate. Recombinant CVN blocked HIV-1 BaL infection of human ectocervical explants with no cytotoxic effects (ref 15). Gel formulations of CVN applied rectally to male macaques protected against challenge by the SIV/HIV-1 virus SHIV89.6P (ref 16). Further demonstration of in vivo efficacy was shown in a vaginal challenge model with female macaques. The macaques were treated with a vaginal gel containing CVN and challenged with SHIV89.6P. Under the challenge conditions of this assay, all placebo-treated and untreated controls (8 of 8) became infected, while 15 of 18 CVN treated macaques were not infected. CVN showed no clinically adverse effects in these in vivo assays.

CVN binds specifically to the highly glycosylated viral envelope protein gp120 and to the functionally analogous SIV proteins sgp130 and sgp140. In contrast, CVN does not bind appreciably to the soluble form of the cellular receptor CD4 (sCD4) or to a battery of other reference proteins. Investigations of CVN interactions by solution biophysical methods with both HIV-1 JRFL and HIV-1 89.6 envelope proteins gp120 and gp41 showed that the interaction of CVN with gp120 is of preferentially higher affinity, in the nM $K_D$ range, with a greater than 1:1 stoichiometry (ref 17). The epitopes on gp120 responsible for CVN binding appear to be predominantly high-mannose glycosylation sites of the Env, specifically terminal Man-α(1-2)manα-moieties on Man-8 and Man-9 glycans, and these appear key to the antagonist properties of the CVN molecule (ref 18-25). The high resolution structure of CVN has been solved by both X-ray crystallography and nuclear magnetic resonance spectroscopy (ref 26-30). These studies have identified carbohydrate binding sites on the CVN molecule. One of these appears to be higher affinity. Mutagenic analysis has shown that the high affinity site by itself is responsible for inhibition of HIV-1 fusion activity by CVN. Nonetheless, there are potential limitations, including amount of CVN production required based on measured in vivo efficacy, reliance on a single site of action and CV-N resistant strains of virus.

Another potential microbicide is the linear peptide 12p1 which was initially isolated from a phage display library and found to inhibit interaction of HIV-1 gp120 with both CD4 and a CCR5 surrogate, mAb 17b (ref 31). There is a direct interaction of 12p1 with gp120, which occurs with a binding stoichiometry of 1:1 (ref 32). The peptide was shown to inhibit the binding of monomeric YU2 gp120 to both sCD4 and 17b at $IC_{50}$ values of 1.1 and 1.6 µM, respectively as determined by SPR analysis. This dual inhibition is a key feature of the action of 12p1. Peptide 12p1 also inhibited binding of these ligands to trimeric envelope glycoproteins, blocked the binding of gp120 to the native co-receptor CCR5, and specifically inhibited HIV-1 infection of target cells in vitro. Analyses of sCD4 saturation of monomeric gp120 in the presence or absence of a fixed concentration of peptide suggest that 12p1 suppression of CD4 binding to gp120 is due to allosteric inhibitory effects rather than competitive inhibition of CD4 binding. Using a panel of gp120 mutants that exhibit weakened inhibition by 12p1, the putative binding site of the peptide was mapped to a region immediately adjacent to, but distinguishable from, the CD4 binding footprint. 12p1 was unable to inhibit binding of sCD4 to a gp120 mutant, S375W, which is believed to resemble the CD4-induced conformation of gp120. The results obtained to date strongly suggest that 12p1 preferentially binds gp120 prior to engagement of CD4, and alters the conformational state of gp120 to a form that has suppressed interactions with receptor ligands (CD4 and CCR5/CXCR4) that are generally believed crucial for viral entry.

Thus, despite the foregoing developments, there is still a need in the art for a retrovirus inhibitor and more specifically for an HIV inhibitor.

All references cited herein are incorporated herein by reference in their entireties.

BRIEF SUMMARY OF THE INVENTION

Accordingly, in one aspect, the invention is a chimeric protein comprising a first sequence coding for cyanovirin, a second sequence coding for 12p1 and a linker covalently connecting the first sequence coding for cyanovirin with the second sequence coding for 12p1, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5 and the second sequence coding for 12p1 is selected from the group consisting of nucleic acid sequence of SEQ ID NO: 6 and nucleic acid sequence of SEQ ID NO: 7.

In certain embodiments, the linker comprises nucleic acid sequence of SEQ ID NO: 8.

In certain embodiments, the linker has at least three repeats of SEQ ID NO: 8. In certain embodiments, the linker has a nucleotide sequence of SEQ ID NO: 7.

In certain embodiments, the linker has at least five repeats of a SEQ ID NO: 8 or corresponds to SEQ ID NO: 9.

In certain embodiments, the chimeric protein has a nucleotide sequence of SEQ ID NO: 10.

In certain embodiments, the chimeric protein has a nucleotide sequence of SEQ ID NO: 11.

In another aspect, the invention is an HIV inhibitor comprising a chimeric protein comprising a first sequence coding for cyanovirin, a second sequence coding for 12p1 and a linker covalently connecting the first sequence coding for cyanovirin with the second sequence coding for 12p1, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5 and the second sequence coding for 12p1 is selected from the group consisting of nucleic acid sequence of SEQ ID NO: 6 and nucleic acid sequence of SEQ ID NO: 7.

In another aspect, the invention is a pharmaceutical composition comprising the HIV inhibitor as described above and a pharmaceutically acceptable carrier.

In another aspect, the invention is a pharmaceutical composition comprising:

(i) an isolated and purified first nucleic acid molecule protein encoding a first sequence coding for cyanovirin, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5; and (ii) an isolated and purified second nucleic acid molecule protein encoding a second sequence coding for 12p1, wherein the second sequence coding for 12p1 is selected from the group consisting of nucleic acid sequence of SEQ ID NO: 6 and nucleic acid sequence of SEQ ID NO: 7, wherein said pharmaceutical composition is effective to prevent, treat or alleviate an HIV infection in a mammal.

In another aspect, the invention is a method of preventing or alleviating an HIV infection, the method comprising providing the pharmaceutical composition comprising the HIV inhibitor as described above and a pharmaceutically acceptable carrier wherein said pharmaceutical composition is provided in an amount effective to prevent, treat or alleviate an HIV infection in a mammal.

In another aspect, the invention is a method of preventing or alleviating an HIV infection, the method comprising providing the pharmaceutical composition comprising:

(i) an isolated and purified first nucleic acid molecule protein encoding a first sequence coding for cyanovirin, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5; and (ii) an isolated and purified second nucleic acid molecule protein encoding a second sequence coding for 12p1, wherein the second sequence coding for 12p1 is selected from the group consisting of nucleic acid sequence of SEQ ID NO: 6 and nucleic acid sequence of SEQ ID NO: 7, wherein said pharmaceutical composition is provided in the amount effective to prevent, treat or alleviate an HIV infection in a mammal.

In another aspect, the invention is a vector comprising the chimeric protein of the invention.

In another aspect, the invention is a host cell containing the vector comprising the chimeric protein of the invention.

In another aspect, the invention is a method of producing a protein, which method comprises expressing a protein in a host cell containing the vector comprising the chimeric protein of the invention. In certain embodiments, the host cell is an autologous or a homologous mammalian cell. In certain embodiments, the host cell is a nonpathogenic bacterium or a nonpathogenic yeast. In certain embodiments, the host cell is a *lactobacillus*.

In another aspect, the invention is an antibody to the chimeric protein of the invention.

BRIEF DESCRIPTION OF SEVERAL VIEWS OF THE DRAWINGS

The invention will be described in conjunction with the following drawings in which like reference numerals designate like elements and wherein:

FIG. 2B is a schematic representation of the constructs used in this paper (not drawn to scale). All constructs contain a pel b secretory sequence and a hexa-histidine tag for purification. The L5 chimera (encoded by SEQ ID NO: 10) contains the peptide 12p1 (SEQ ID NO: 12 or 13) c-terminal to the CVN domain (SEQ ID NO: 2) with an intervening linker of five repeats of Gly4Ser (encoded by SEQ ID NO: 9). The construct L5-S12p1 contains the non-sense peptide (WRIM-MIPSEANN; SEQ ID NO: 14) c-terminal to the CVN domain and contains a linker of five repeats of (Gly)4Ser (encoded by SEQ ID NO: 9).

DETAILED DESCRIPTION OF THE INVENTION

Figure 1:
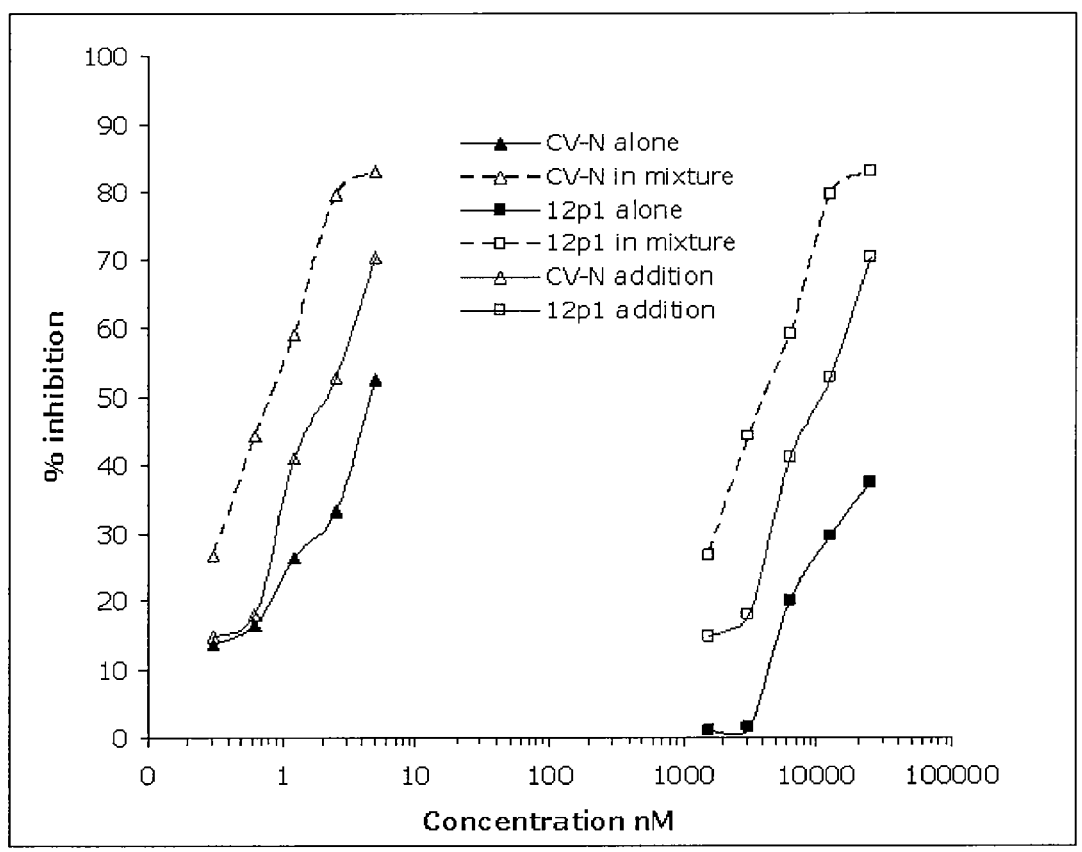
FIG. 1 is a graph demonstrating synergy of using 12p1 with CV-N. Inhibition effects are shown as a function of dose of CV-N, 12p1, or mixture of the two. The "mixture" data were obtained with mixtures of lowest concentration of CV-N with the lowest dose of 12p1, etc. to highest dose CV-N with the highest dose of 12p1. The curves are also shown for the dose response expected if the effects were simply additive. These data show that mixing 12p1 with CV-N does not interfere with the latter and instead synergizes positively.

This invention was prompted by the idea to form a chimeric protein entry inhibitor that combines the action two gp120-targeting molecules, an allosteric peptide inhibitor 12p1 and a higher affinity carbohydrate-binding protein cyanovirin (CVN). The invention was driven by a desire to develop a novel HIV inhibitor which can overcome potency limits and potential virus mutational resistance for either 12p1 or CVN alone. Inventors created a chimeric protein which utilizes the high affinity binding of CVN and the unique allosteric inhibition of 12p1. CVN was chosen as a fusion partner for several reasons: (i) CVN binds to gp120 with high affinity and inhibits HIV from a broad range of clades and tropisms; (ii) CVN binds to high mannose residues in regions that don't appear to overlap with domains traditionally targeted for inhibition as determined by its inability to compete with a variety of monoclonal antibodies to gp120 or sCD4; (iii) CVN is currently under investigation as a topical microbicide. (iv) CVN retains its antiviral ability after treatment with denaturants, heat and detergents and therefore may also be able to function after the addition of a long polypeptide chain to one of its termini. 12p1 was chosen because (i) it inhibits in a manner distinct from CVN, (ii) is small and (iii) has no disulfide bonds that could potentially lead to misfolding and aggregation.

The chimeric protein of the invention can be shown to inhibit a virus, specifically a retrovirus, such as the human immunodeficiency virus, i.e., HIV-1 or HIV-2. The chimeric protein of the present invention can be used to inhibit other retroviruses as well as other viruses. Examples of viruses that can be treated in accordance with the present invention include, but are not limited to, Type C and Type D retroviruses, HTLV-1, HTLV-2, HIV, FLV, SIV, MLV, BLV, BIV, equine infectious virus, anemia virus, avian sarcoma viruses, such as Rous sarcoma virus (RSV), hepatitis type A, B, non-A and non-B viruses, arboviruses, varicella viruses, measles, mumps and rubella viruses In initial mixing experiments, it was demonstrated that these inhibitors do not interfere with each other and show functional synergy in inhibiting viral cell infection when used together. In certain embodiments of the invention, the chimeric protein fusion inhibitor comprises 12p1 linked to the C-terminal domain of CVN through a flexible linker of one through seven penta-peptide repeats of glycine and serine. The chimerae with five repeats of the linker termed, L5, binds to gp120 from a variety of clades and tropisms. Advantageously, the chimera exhibits increased inhibition of gp120 binding to receptor CD4, co-receptor surrogate mAb 17b and gp120 antibody F105. Binding inhibition by chimera reflects both the high affinity of the CVN domain and the allosteric action of the 12p1 domain. This enhanced inhibition is lost in constructs where the sequence of 12p1 is scrambled, rendering it inactive. This work laid a background for creating high potency chimeras, as well as non-covalent mixtures, as leads for HIV-1 envelope antagonism that can overcome potency limits and potential virus mutational resistance for either 12p1 or CVN alone.

Chimeras of CVN and 12p1 or variants thereof present a model for targeting gp120 at two discrete sites, by two different modes of inhibition and with increasing potency versus either component alone. A chimera of the invention combines the high affinity suppression of viral activity by CVN with the allosteric suppression of viral envelope binding to both CD4 and co-receptor by 12p1. Furthermore, since the binding sites for CVN and 12p1 both reside within gp120 but at sterically separate locations, the combination of these two agents as a covalent chimera increases the ability to overcome resistance mutations at individual binding sites for either component alone.

In certain embodiments, CVN and 12p1 or variants thereof are covalently linked in a chimera to be administered in a pharmaceutical composition to prevent, treat or alleviate HIV infection in a mammal. Thus, in one aspect, the invention is an HIV inhibitor comprising a chimeric protein comprising a first sequence coding for cyanovirin, a second sequence coding for 12p1 and a linker covalently connecting the first sequence coding for cyanovirin with the second sequence coding for 12p1, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5 and the second sequence coding for 12p1 is selected from the group consisting of nucleic acid sequence of SEQ ID NO: 6 and nucleic acid sequence of SEQ ID NO: 7. In another aspect, the invention is a pharmaceutical composition comprising the HIV inhibitor as described above and a pharmaceutically acceptable carrier.

In certain embodiments, CVN and 12p1 or variants thereof are not covalently linked but combined as a mixture to be administered in a pharmaceutical composition to prevent, treat or alleviate HIV infection in a mammal. Thus in one aspect, the invention is a pharmaceutical composition comprising: (i) an isolated and purified first nucleic acid molecule protein encoding a first sequence coding for cyanovirin, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5; and (ii) an isolated and purified second nucleic acid molecule protein encoding a second sequence coding for 12p1, wherein the second sequence coding for 12p1 is selected from the group consisting of nucleic acid sequence of SEQ ID NO: 6 and nucleic acid sequence of SEQ ID NO: 7, wherein said pharmaceutical composition is effective to prevent, treat or alleviate an HIV infection in a mammal.

DEFINITIONS

Cyanovirin-N

CVN is an 11 kDa protein originally isolated from the cyanobacterium, *Nostic ellipsosporum* (ref 14). Inactivated a broad spectrum of HIV clades including A, B, C, D and circulating recombinant forms. Cyanovirin-N specifically binds with nanomolar affinity to mammalian high mannose oligosaccharides, D1D3 isomer of Man8GlcNAc2 (Man8 D1D3) and Man9GlcNAc2 (Man 9). CVN is currently in development as a female controlled microbicide.

The terms "cyanovirin," "cyanovirin-N" or its abbreviation CVN is used herein to generically refer to a native antiviral protein isolated from *Nostoc ellipsosporum* ("native cyanovirin") and any functionally equivalent protein or derivative thereof. In the context of the present invention, such a functionally equivalent protein or derivative thereof (a) contains a sequence of at least nine (preferably at least twenty, more preferably at least thirty, and most preferably at least fifty) amino acids directly homologous with (preferably the same as) any subsequence of nine contiguous amino acids contained within a native cyanovirin (especially cyanovirin-N), and (b) is antiviral, in particular capable of specifically binding to a virus, more specifically a primate immunodeficiency virus, more specifically HIV-1, HIV-2, or SIV, or to an infected host cell expressing one or more viral antigen(s), more specifically an envelope glycoprotein, such as gp120, of the respective virus. In addition, such a functionally equivalent protein or derivative thereof can comprise the amino acid sequence of a native cyanovirin, particularly cyanovirin-N (see SEQ ID NO: 2), in which 1-20, preferably 1-10, more preferably 1, 2, 3, 4, or 5, and most preferably 1 or 2, amino acids have been removed from one or both ends, preferably from only one end, and most preferably from the amino-terminal end, of the native cyanovirin.

Cyanovirin of the invention preferably comprises an amino acid sequence that is substantially homologous to that of an antiviral protein from *Nostoc ellipsosporum*, specifically a native cyanovirin, particularly cyanovirin-N. In the context of the cyanovirins of the present invention, the term "substantially homologous" means sufficient homology to render the cyanovirin antiviral, preferably with antiviral activity characteristic of an antiviral protein isolated from *Nostoc ellipsosporum*. There preferably exists at least about 50% homology, more preferably at least about 75% homology, and most preferably at least about 90% homology.

Thus, in the present invention, a first nucleic acid sequence or a cyanovarin coding sequence comprises at least one of a sequence of SEQ ID NO:1, SEQ ID NO:2, SEQ ID NO:3, SEQ ID NO:4 or SEQ ID NO:5.

It will be apparent to one skilled in the art that a partial cyanovirin-N gene codon sequence will likely suffice to code for a fully functional, i.e., antiviral, such as anti-HIV, cyanovirin. A minimum essential DNA coding sequence(s) for a functional cyanovirin can readily be determined by one skilled in the art, for example, by synthesis and evaluation of sub-sequences comprising the native cyanovirin, and by site-directed mutagenesis studies of the cyanovirin-N DNA coding sequence.

Using an appropriate DNA coding sequence, a recombinant cyanovirin can be made by genetic engineering techniques (see, e.g., for general background, Nicholl, in An Introduction to Genetic Engineering, Cambridge University Press: Cambridge, 1994, pp. 1-5 & 127-130). For example, a *Nostoc ellipsosporum* gene or cDNA encoding a cyanovirin can be identified and subcloned. The gene or cDNA can then be incorporated into an appropriate expression vector and delivered into an appropriate protein-synthesizing organism (e.g., *E. coli, S. cerevisiae, P. pastoris*, or other bacterial, yeast, insect, or mammalian cell), where the gene, under the control of an endogenous or exogenous promoter, can be appropriately transcribed and translated. Such expression vectors (including, but not limited to, phage, cosmid, viral, and plasmid vectors) are known to those skilled in the art, as are reagents and techniques appropriate for gene transfer (e.g., transfection, electroporation, transduction, micro-injection, transformation, etc.). Subsequently, the recombinantly produced protein can be isolated and purified using standard techniques known in the art (e.g., chromatography, centrifugation, differential solubility, isoelectric focusing, etc.), and assayed for antiviral activity.

Alternatively, a native cyanovirin can be obtained from *Nostoc ellipsosporum* by non-recombinant methods and sequenced by conventional techniques. The sequence can then be used to synthesize the corresponding DNA, which can be subcloned into an appropriate expression vector and delivered into a protein-producing cell for en mass recombinant production of the desired protein.

Peptide 12p1

12p1 is a linear peptide, RINNIPWSEAMM (SEQ ID NO: 12; encoded by SEQ ID NO: 6) which was discovered by a phage display library (ref 31). 12p1 has the following structure:

12p1 inhibits CD4, 17b co-receptor surrogate, and CCR5 interaction by binding to monomeric and trimeric gp120. Binding site mapping via mAb-binding assays indicated that 12p1 has different effects upon binding of gp120 to conformational and non-conformationally dependent antibodies. This hints towards the binding site being present in a particular gp120 conformational state. 12p1's mode of inhibition appears to be allosteric in nature, as inferred from the inability of excess sCD4 to overcome the inhibitory effect of a set concentration of the peptide.

Variants of 12p1 would include a sequence consisting of I N N I P W S (SEQ ID NO: 13; encoded by SEQ. ID NO: 7).

Possible options for useful chemical modifications of a cyanovirin, 12p1 or a chimera prepared from these compounds include, but are not limited to, (a) olefin substitution, (b) carbonyl reduction, (c) D-amino acid substitution, (d) N alpha-methyl substitution, (e) C alpha-methyl substitution, (f) C alpha-C'-methylene insertion, (g) dehydro amino acid insertion, (h) retro-inverso modification, (i) N-terminal to C-terminal cyclization, and (j) thiomethylene modification. Cyanovirins, 12p1 or a chimera prepared from these compounds also can be modified by covalent attachment of carbohydrate and polyoxyethylene derivatives, which are expected to enhance stability and resistance to proteolysis (Abuchowski et al., in Enzymes as Drugs, Holcenberg et al., eds., John Wiley: New York, 1981, pp. 367-378).

Linker

Figure 2A:
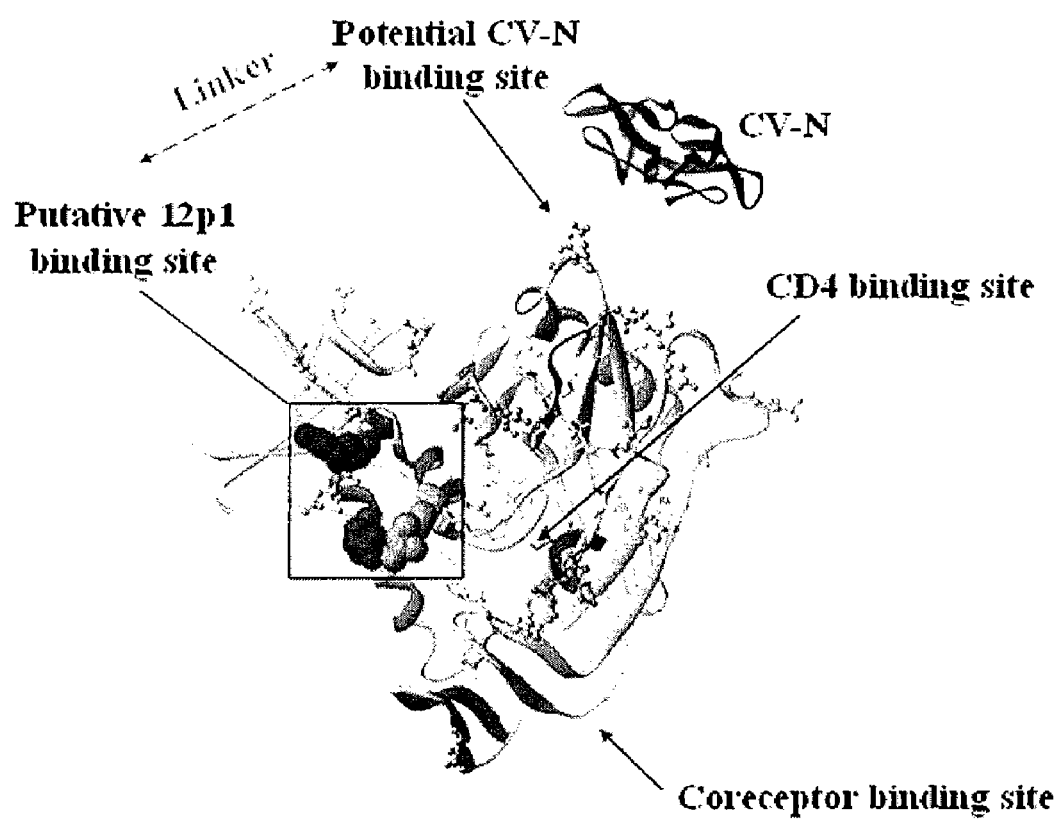
FIG. 2A shows HIV-1YU2 gp120 denoting various ligand binding sites. Potential glycosylation sites that could be sites of CV-N binding are shown as green ball and stick. The three residues found important for 12p1 binding (Lys97, Glu102, and Arg476) are in space filling representations.

Since the precise binding sites for CVN are not known, inventors could not estimate the distance between the binding sites of the two compounds in the known high resolution structure of gp120 (FIG. 2A). A further complication was the predicted 5:1 binding ratio of CVN, unlike the 1:1 binding ratio of 12p1. In one embodiment, the linker is a 25 amino acid linker which acts as a starting inter-domain spacer (SEQ ID NO: 9). The amino acid composition of the linkers is also an important parameter to consider since it will determine secondary structural characteristics of the spacer. The linker useful in this invention preferably contains a combination of glycine and serine residues which provides flexibility and protease resistance. Rigidity of the linker can also vary.

In a preferred embodiment, the linker comprises aminoacids which induce flexible conformation. For example, the linker can have one to seven penta-peptide repeats of glycine and serine (SEQ ID NO: 8). In other embodiments of the invention, the linker can contain amino acids that induce a rigid conformation. In other embodiments, the linker can be a polymer.

Chimeric Proteins of the Invention

In one aspect, the invention is a chimeric protein comprising a first sequence coding for cyanovirin, a second sequence coding for 12p1 and a linker covalently connecting the first sequence coding for cyanovirin with the second sequence coding for 12p1, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5 and the second sequence coding for 12p1 is selected from the group consisting of nucleic acid sequence of SEQ ID NO: 6 and nucleic acid sequence of SEQ ID NO: 7. The chimeric protein of the invention comprises 12p1 linked to the C-terminal domain of cyanovirin via a linker prepared by methods known in the art.

In a preferred embodiment of the invention, the chimera is a construct (SEQ. ID NO: 10) in which the N-terminal domain of 12p1 (SEQ ID NO: 6) is linked to the C-terminal domain of CVN (SEQ ID NO: 5) via a long flexible linker of five Gly$_4$Ser repeats (SEQ. ID NO: 9). See FIG. 2B.

In certain embodiments, the chimera, designated L5, contains a hexa-histidine tag on its C-terminus both for ease of purification and for confirming the accessibility of the C-terminal 12p1 domain (SEQ ID NO: 15).

Also designed was a chimera in which the 12p1 sequence was scrambled (SEQ ID NO: 14), rendering it non-functional (L5-S12p1). The latter construct was derived from the L5 chimera and was identical to it in all aspects except binding functionality.

Figure 3:
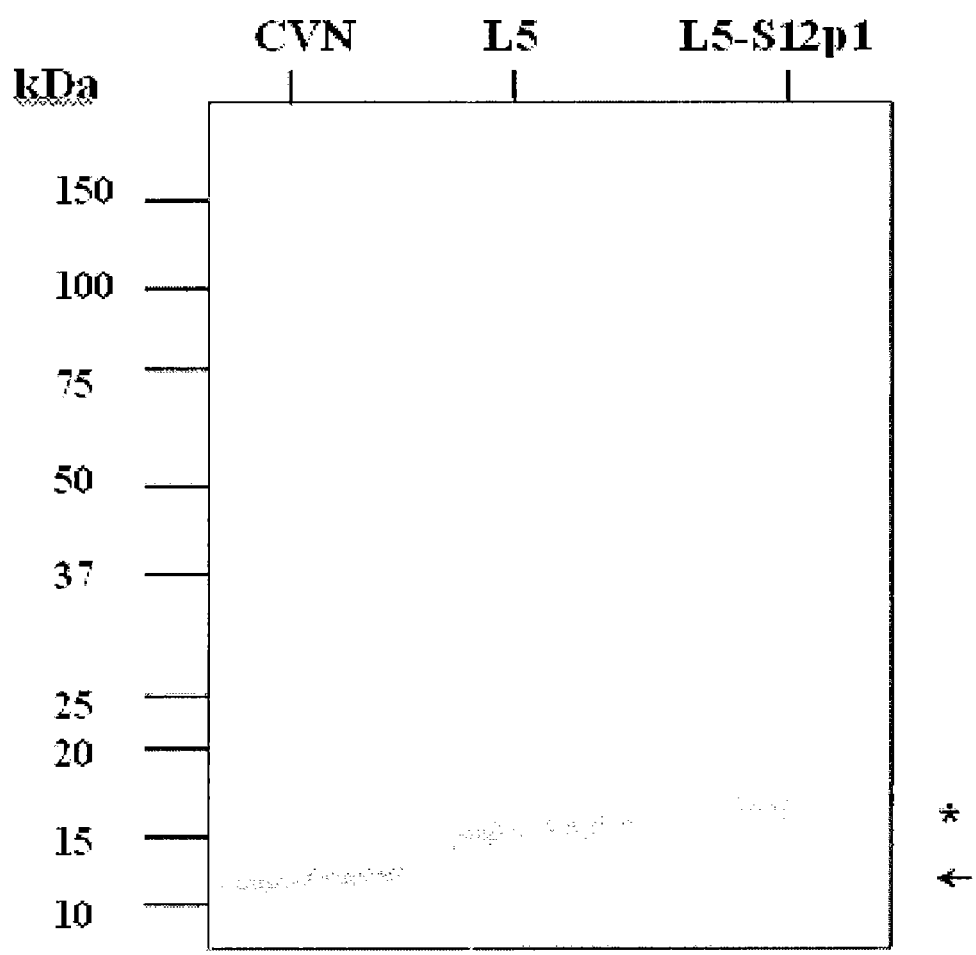
FIG. 3 is a picture of a gel demonstrating expression and purity of chimeras. All constructs were isolated by osmotic shock and purified over a Nickle-NTA column. The arrowhead indicates the position of the CVN band (11 kDa) and the asterisk indicates the position of the chimerae (15 kDa). Samples were separated on a 4-20% gel under reducing conditions and stained with Simply Blue (Invitrogen) Coomassie stain.
Figure 4A:
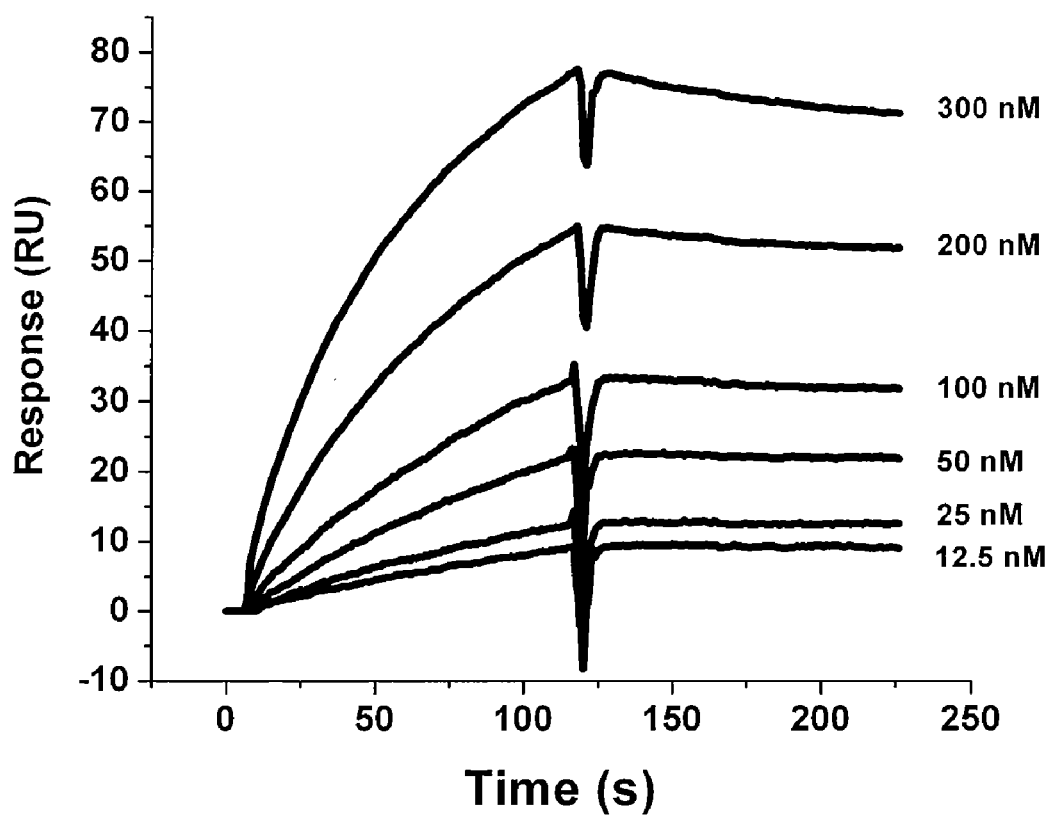
FIG. 4A is a graph demonstrating Biosensor analysis of CVN binding to immobilized HIV-1YU2 gp120.
Figure 4B:
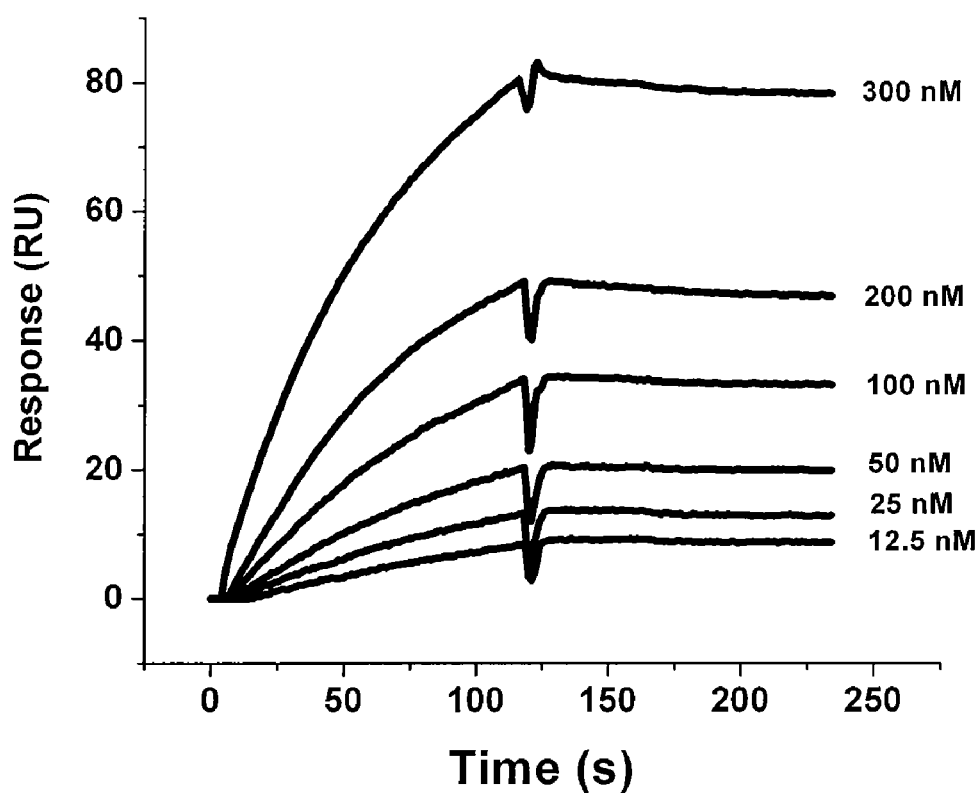
FIG. 4B is a graph demonstrating Biosensor analysis of the L5 (4B) chimera binding to immobilized HIV-1YU2 gp120.
Figure 4C:
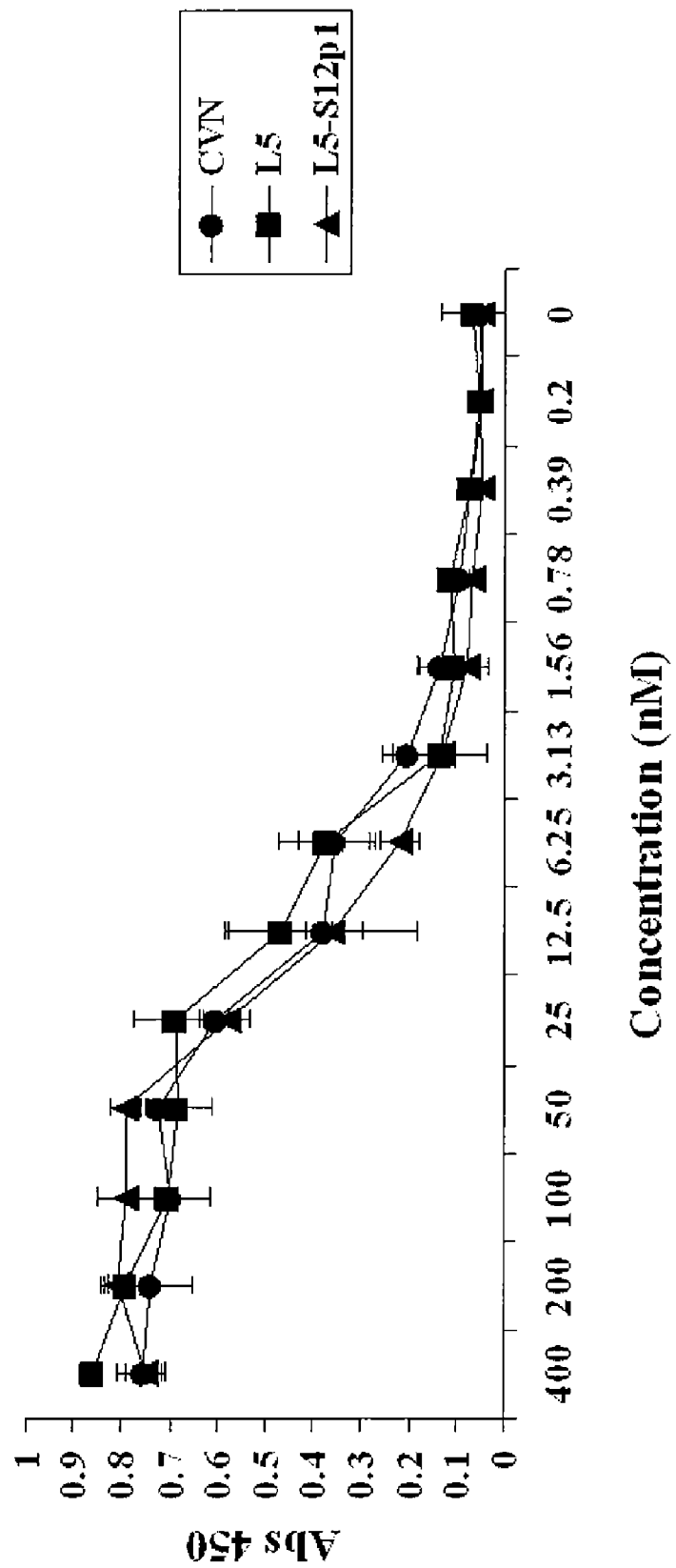
FIG. 4C are representative sensorgrams of the interaction of CVN or L5 with sensor chip immobilized YU2-gp120. CVN or L5 was passed over the chip at concentrations of 300, 200, 100, 50, 25 and 12.5 nM. ELISA assay of serial dilutions of CVN (circles), L5 (squares) or L5-S12p1 (triangle) were added to 100 ng of bound YU2 gp120. The extent of binding was detected by polyclonal anti-CVN. Points are averages of triplicate determinations after the subtraction of non-specific binding to BSA. Error bars indicate standard deviation.
Figure 4D:
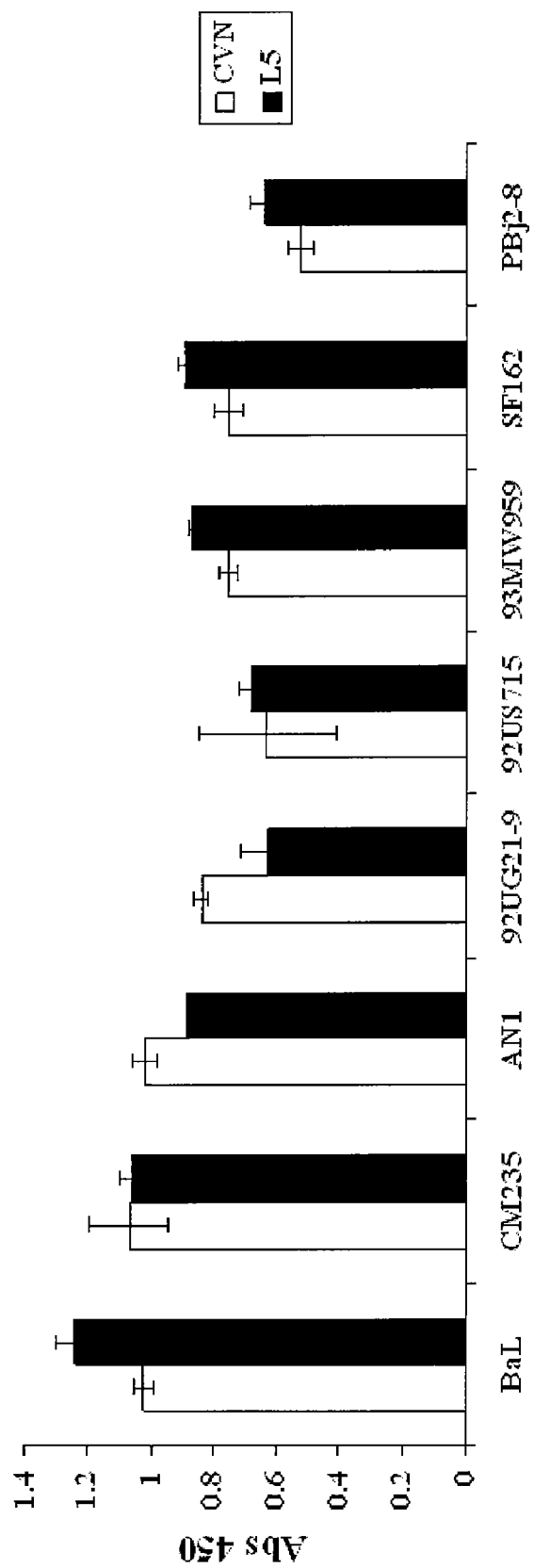
FIG. 4D is a bar graph depicting ELISA assay of CVN or the L5 chimera binding to gp120 of a variety of clades and tropisms. In ELISA experiments, 100 ng of the indicated gp120 was adsorbed onto an ELISA plate followed by the addition of 50 nM of either CVN (white bars) or the L5 chimera (black bars). The extent of binding was detected with a polyclonal antibody against CVN. Bars represent triplicate determination after the subtraction of non-specific binding to BSA. Error bars indicate one standard deviation.

CVN, L5 and L5-S12p1 were expressed in E. coli using the induction conditions optimized in Colleluori et al (ref 37). All constructs were expressed in the periplasmic fraction, isolated by osmotic shock and purified over a NiNTA column. The similar high degree of homogeneity of all purified expressed proteins was determined by Coomassie stain (FIG. 3) and western blot.

The constructs can be cloned into the pET30b+prokaryotic expression system and transformed into BL21 (DE3) strain of E. coli.

Methods of making the chimeric protein of the invention include:

(a) providing a first sequence coding for cyanovirin and a second sequence coding for 12p1 and a linker, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5 and the second sequence coding for 12p1 is selected from the group consisting of nucleic acid sequence of SEQ ID NO: 6 and nucleic acid sequence of SEQ ID NO: 7.

(b) ligating the linker and the second nucleic acid sequence (a 12p1 coding sequence) to a C-terminal in the first sequence coding for cyanovirin to form a vector comprising the chimeric protein;

(c) transforming the vector into appropriate cells (e.g., BL21 (DE3)) and grow until the absorbance at 600 reach a desired value (e.g., 1.2) and optionally induce the culture (e.g., 1 mM IPTG for 2 hours); and (d) isolating the chimeric protein from the periplasmic space using osmotic shock and purified over nickel NTA agarose column to obtain the desired chimeric protein in substantially pure form.

In the preferred embodiment, the L5 chimera was constructed using standard recombinant DNA techniques. CVN was amplified from a plasmid template using the forward primer 5'pelb and the reverse primer 3CVN in order to insert a pel b secretory sequence and eliminate the stop codon. CVN was ligated into pET30b+vector generating pCVN. The linker, 12p1 (or scrambled 12p1) cassettes were synthesized as separate oligonucleotides (Invitrogen) and ligated in frame with the C-terminal domain of CVN generating pL5 (or pL5-S12p1). The entire construct was amplified with the forward primer 5'pelb and a reverse primer containing a hexa-histidine tag (3'12p1 His) generating pL5H is. The construct was sequenced by DNA Sequencing Facility prior to transformation into BL21 (DE3) strain of *Eschericia coli.*

L5 was stable over prolonged periods and multiple freeze thaw cycles. The chimera was found to bind to gp120 with similar affinity to CVN alone as determined by both ELISA and Biacore assays (FIGS. 4A-D). This indicates that CVN is able to tolerate the addition of a long polypeptide tail onto its C-terminal domain with no disruption of its ability to bind gp120 with high affinity. While we did not expect and did not observe an enhancing effect of the 12p1 domain on the overall gp120 binding affinity of the chimera due to the substantially weaker binding affinity of 12p1, the chimera nonetheless exhibited important new binding properties to the HIV-1 Env. In particular, the chimera was able to exhibit the combined interaction-inhibiting activities unique to the 12p1 domain with the much stronger affinity and slow dissociation rate of the CVN domain. This was evident in the inhibition of binding to CD4, 17b and F105 (FIGS. 5, 6). This pattern of inhibition is lost when the 12p1 domain is scrambled. These observations demonstrate that the two domains of the chimera can bind at the same time to gp120, with the result of a high affinity, allosteric inhibitor that has the potential to suppress both host cell receptor interactions of the viral envelope. The wide specificity of the CVN moiety (FIGS. 4A-D) suggests that the chimera has potential usefulness across diverse variants of the HIV-1 virus. Broad specificity has recently been observed for variants of 12p1 peptide (Cocklin S. et al (2007) J. Virol. 81(7):3645), reinforcing further the opportunity to employ the antagonist potential of the chimera to inhibit diverse viral forms, even those in which one of the target epitopes (either carbohydrate for CVN or binding footprint for 12p1) is mutated. Direct binding of CVN or the chimera to YU2 variant of gp120

Inventors initially confirmed that the L5 chimera retains the high affinity binding to gp120 characteristic of the CVN domain through both ELISA and biosensor analysis. The binding to CVN or the L5 chimera to immobilized gp120 was analyzed on a Biacore 3000 SPR optical biosensor. Approximately 250 RUs of either YU2 gp120 or the non-specific control antibody 2B6R were immobilized to a CM5 dextran chip by amine coupling. Either CVN or L5 were passed over the chip at a flow rate of 30 μl/min for one minute association; the dissociation phase was for two minutes at the same flow rate. Signals from the reference 2B6R flow cell were used to correct for non-specific interactions and bulk effects (FIGS. 4A, B). Biosensor response is expected to be proportional to molecular weight, with a maximum response of 33 RU for CVN binding and 45 RU for L5 binding assuming 1:1 binding stoichiometry. CVN was found to bind with a 95 RU signal at 300 nM indicating a 3:1 stoichiometry, while L5 bound with 90 RU signal at 300 nM indicative of a 2:1 stoichiometry. While these stoichiometries do not approach the 5:1 value previously reported for CVN, the concentrations used in this study were below the saturation levels for each complex to prevent non-specific aggregation commonly seen at elevated levels. The results suggest that both CVN and L5 bind to gp120 multivalently, and that L5 binds at a somewhat lower stoichiometry than CVN.

ELISA assays were also performed to detect the binding of CVN or the chimera to YU2 gp120 (FIG. 4C). YU2 was adsorbed to a 96-well EIA/RIA plate overnight at 4° C. The wells were blocked and washed prior to the addition of serial dilutions of CVN, L5 or L5-S 12p1 for one hour at room temperature. The extent of binding was determined by a polyclonal antibody directed against CVN. The chimera retained its ability to bind to gp120 at concentrations equivalent to that of unmodified CVN. This indicates that the addition of 37 amino acids onto the c-terminal domain of CVN does not alter its ability to bind to gp120, supporting its potential as for fusion inhibition. The equilibrium dissociation constant $K_D$ for binding of CVN to YU2 has been reported as 11 nM, as compared to 3.6 μM for 12p1[38]. Based on these affinity values, one would expect that binding of the chimera to gp120 would be primarily directed by the CVN domain of the chimera.

CVN has the ability to inhibit X4-tropic, R5-tropic and dual tropic primary isolates and laboratory adapted strains of HIV[20,44]. We therefore tested the ability of the chimera to bind to the gp120s from a variety of strains of HIV-1 of diverse clades and tropisms. These included HIV-$1_{SF162}$ (Clade B), HIV-$1_{93MW959}$ (Clade C), HIV-$1_{92UG21-9}$ (Clade A), HIV-$1_{92US715}$ (Clade B), $SIV_{PBj2-8}$ from Jim Arthos at NIAID, AN1 (an ancestral clade B HIV provided by Jim Mullins[45], HIV-$1_{BaL}$ (clade B), HIV-$1_{CM235}$ (circulating recombinant CRF01-AE obtained from Protein Sciences, Corporation via the NIAID AIDS Reference and Reagent Program). Both the L5 chimera and CVN behaved equivalently with all strains tested (FIG. 4D). The diverse HIV-1 variant specificity hints at their potential for the development of a topical microbicide against stains of HIV that afflict sub-Saharan Africa and other areas of high AIDS occurrence.

Viral Synergy Analysis

Although it is known that CVN binds to high mannose groups on the heavily glycosylated gp120, the specific binding site is unknown. Therefore, inventors initially screened for the ability of CVN and 12p1 to bind to gp120 simultaneously and inhibit viral infection without interfering with each other. These assays were performed by the incubation of the indicated doses of CVN and 12p1 alone or in combination with HIV-1 BaL for one hour prior to the addition of PM-1 cells. Viral replication was determined by gp120 ELISA after a seven day incubation. Dose response curves from the mean of three independent experiments are given in FIG. 1. From these and the additional data, a synergy index for the combination was found to be in the 0.3-0.5 range, compared to a scale of 0.1-0.3 for strong synergism, 0.3-0.7 for synergism, 0.7-0.85 for moderate synergism, 0.85-0.9 for slight synergism and 1.10-1.20 for nearly additive. Even though the synergism shown by these results is modest, it must be borne in mind that CVN has a far greater affinity than 12p1, therefore any effect in non-covalent mixtures using 12p1 is significant. Graphical evidence for how 12p1 can boost the activity of CVN can be seen in FIG. 1 left by comparing the values of % inhibition observed for CVN at the two lowest concentrations either alone (closed triangles) or with CVN at the same two lowest concentrations but with the two lowest concentrations of 12p1 (16-31 µM) added (open triangles). Even though 12p1 at those latter concentrations shows only small inhibitory effect on its own, the presence of 12p1 with CVN significantly boosts efficacy in the mixture by a factor of close to 2-fold. These results indicate that not only can CVN and 12p1 bind gp120 simultaneously but also appear to act to synergistically enhance viral inhibition.

Figure 5A:
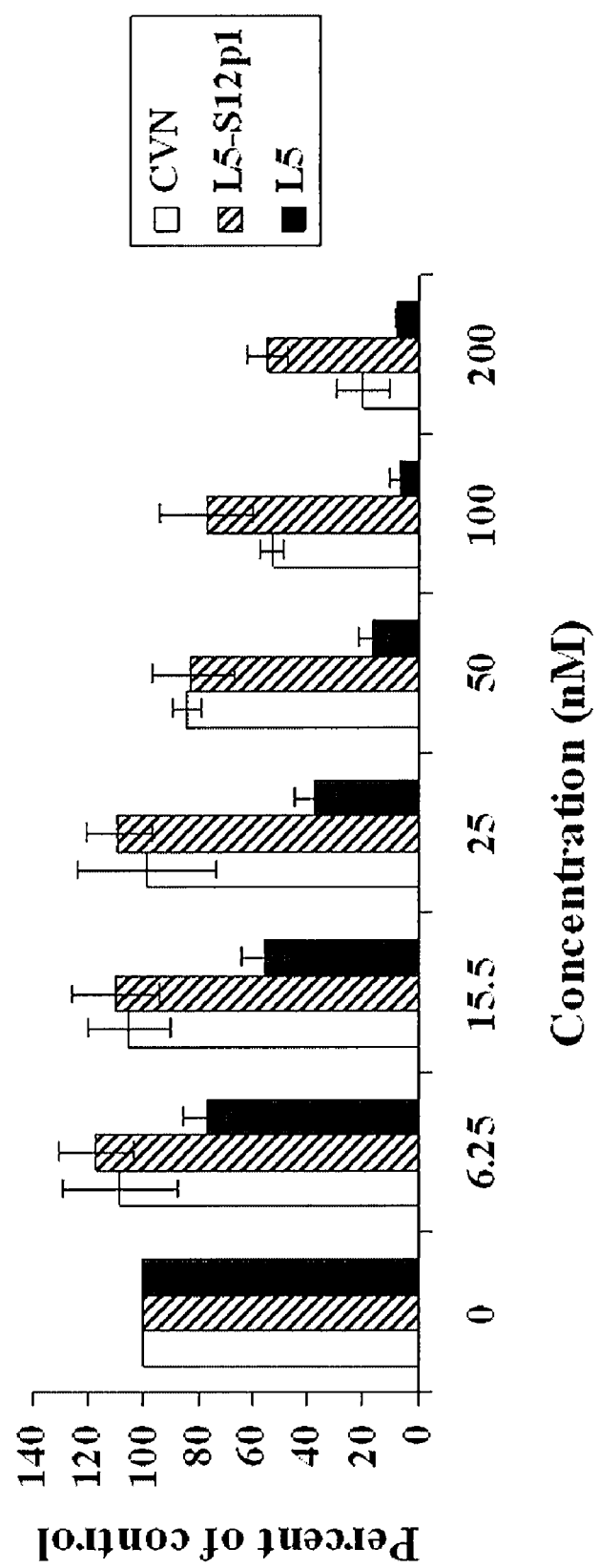
FIGS. 5A-5B are bar graphs demonstrating inhibition of sCD4 or the co-receptor surrogate mAb 17b interaction with YU2 gp120. Monomeric HIV-1YU2 gp120 was adsorbed onto ELISA plates prior to the addition of increasing doses of CVN, L5, L5-S12p1 or unlinked CVN and 12p1 incubated with either 0.5 µg/ml sCD4 (FIG. 5A) or 2 µg/ml 17b (FIG. 5B).

CVN inhibits the interaction of cell associated CD4 with gp120 but has limited effect upon the interaction between soluble CD4 (sCD4) and gp120[46,47]. In contrast, 12p1 can inhibit the interaction of sCD4 with gp120 with an $IC_{50}$ value of 1.1 µM[38]. The ability of the L5 chimera to inhibit CD4 binding to gp120 was investigated. YU2 gp120 was immobilized onto a 96 well ELISA plate overnight. The plate was blocked, and increasing doses of CVN, L5 or L5-S12p1 combined with 0.5 µg/ml sCD4 were added. The extent of binding was detected with a polyclonal antibody against CD4. The data are represented as percent of uninhibited after non-specific binding to BSA was subtracted out (FIG. 5A). The data demonstrate that the L5 chimera can inhibit CD4-gp120 interaction more potently than CVN alone. This enhanced inhibition is lost when the 12p1 domain of the chimera is scrambled.

Figure 5B:
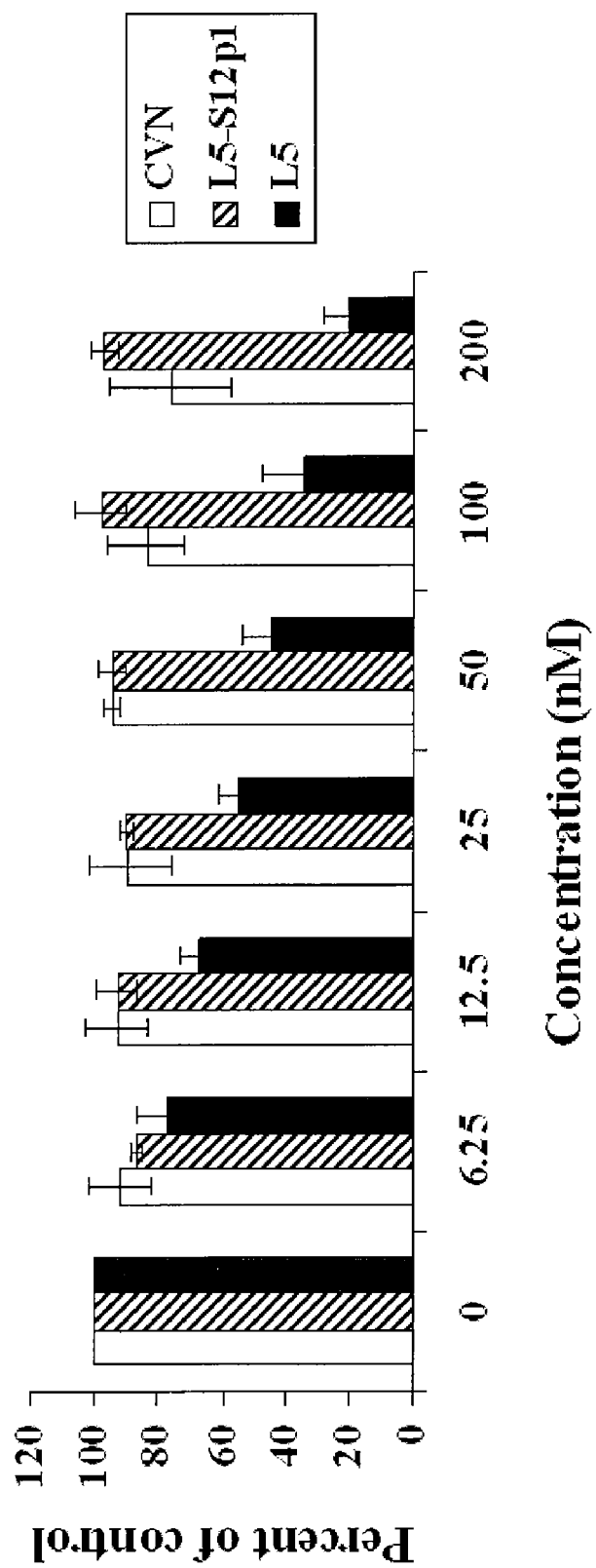

The monoclonal antibody 17b binds to a CD4 induced conformation and can be used as a surrogate for co-receptor binding[48,49] CVN cannot inhibit this interaction[46] while 12p1 inhibits the interaction with an $IC_{50}$ value of 1.6 µM[38], The ability of the L5 chimera to inhibit this interaction was determined through an ELISA. The L5 chimera could inhibit the interaction between 17b and gp120 with an $IC_{50}$ value of 38 nM while neither CVN nor L5-S12p1 had any effect (FIG. 5B). The inability of the L5-S12p1 chimera to inhibit this interaction indicates that the greatly enhanced 17b binding antagonism function is imparted specifically by the 12p1 domain and is not due to either a contaminant or non-specific interaction of the linker domain. Strikingly, this inhibition occurs at a dose that reflects the high affinity binding of the CVN domain of the chimera. The L5 chimera inhibits both the sCD4 and 17b interaction with gp120 at doses at which neither CVN nor 12p1 has an effect. These results demonstrate that both domains of the chimera are able to bind gp120 simultaneously. The chimera has the unique inhibitory properties of 12p1 with the high affinity binding of CVN.

Inhibition by CVN or the Chimera with mAb F105 and 2G12

Figure 6A:
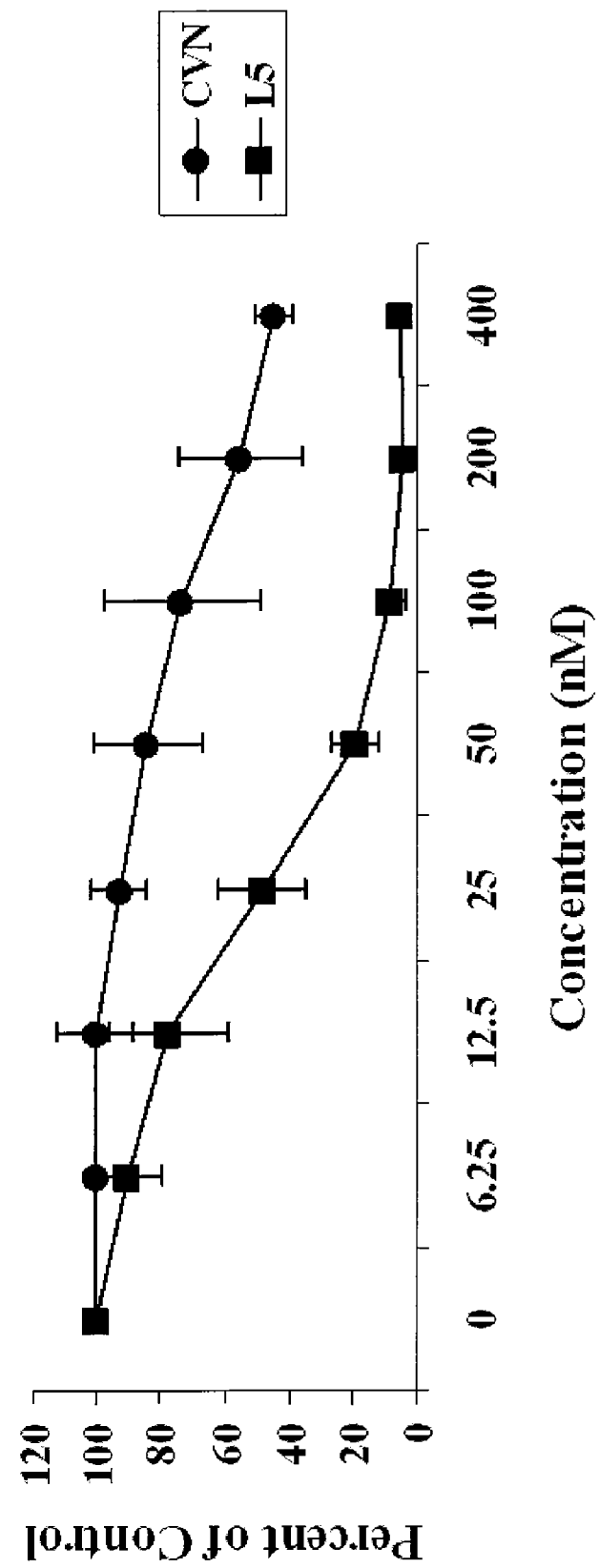
FIGS. 6A-6B are graphs demonstrating competition of CVN or L5 with mAbs F105 (Left) and 2G12 (Right) to gp120. Monomeric HIV-1YU2 gp120 was adsorbed onto ELISA plates overnight prior to blocking with 1% BSA. Increasing doses of CVN (circles) or L5 (squares) was combined with a 1:20,000 dilution of F105 (FIG. 6A) or 50 µg/ml 2G12 (FIG. 6B) was added for one hour at room temperature.
Figure 6B:
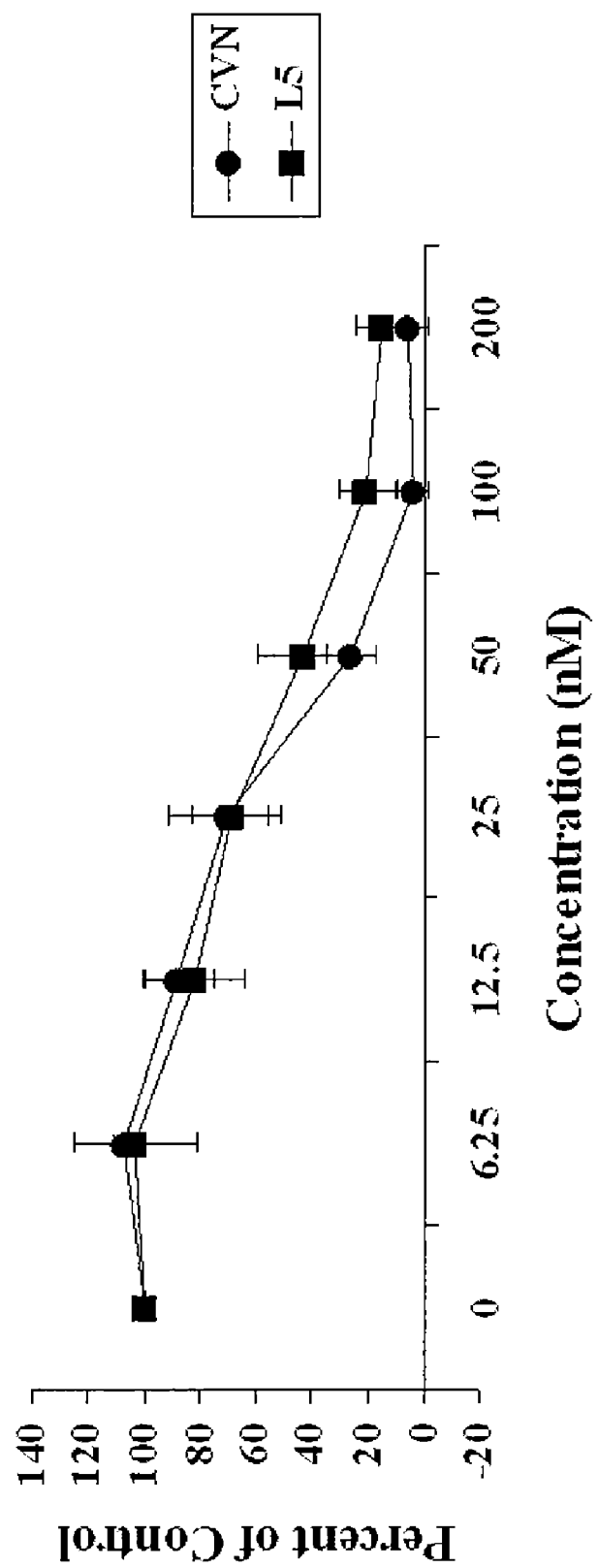

An additional and clear-cut measure of 12p1's binding function in the chimera was determined, as shown in FIGS. 6A-B, by the ability of the chimera to inhibit gp120 binding to the monoclonal antibody F105[50-52]. This antibody recognizes the conformationally-flexible, CD4-unliganded form of gp120[53]. CVN has minimal effect on F105 binding to gp120[46] while 12p1 inhibits the F105-gp120 interaction[38]. mAb 2G12 was used as a negative control, since previous data have shown[38] that binding of 12p1 to gp120 would not be expected to affect binding to this antibody. Strikingly, the suppression of F105 binding was found to occur at nM concentrations[46] or CVN which has a more muted effect on F105 binding to gp120[54]. This dose-response behavior thus reflects both the high affinity binding of CVN to gp 120 and the inhibitory effect of 12p1. In contrast, the chimera as well as CVN show the expected competition of gp120 binding to immobilized 2G12 antibody, the latter of which binds to carbohydrate moieties similar to sites for CVN[46].

In another aspect, the invention is a method of preventing or alleviating an HIV infection, the method comprising providing the pharmaceutical composition comprising the HIV inhibitor as described above and a pharmaceutically acceptable carrier wherein said pharmaceutical composition is provided in an amount effective to prevent, treat or alleviate an HIV infection in a mammal.

In another aspect, the invention is a method of preventing or alleviating an HIV infection, the method comprising providing the pharmaceutical composition comprising:

(i) an isolated and purified first nucleic acid molecule protein encoding a first sequence coding for cyanovirin, wherein the first sequence coding for cyanovirin is selected from the group consisting of (a) at least nine contiguous amino acids of SEQ ID NO: 2, (b) nucleic acid sequence of SEQ ID NO: 1, (c) nucleic acid sequence of SEQ ID NO: 3, (d) amino acid sequence of SEQ ID NO: 4, and (e) nucleic acid sequence of SEQ ID NO: 5; and (ii) an isolated and purified second nucleic acid molecule protein encoding a second sequence coding for 12p1, wherein the second sequence coding for 12p1 is selected from the group consisting of nucleic acid sequence of SEQ ID NO: 6 and nucleic acid sequence of SEQ ID NO: 7, wherein said pharmaceutical composition is provided in the amount effective to prevent, treat or alleviate an HIV infection in a mammal.

The appropriate delivery system for a given chimeric protein will depend upon its particular nature, the particular clinical application, and the site of drug action. As with any protein drug, oral delivery of a chimeric protein of the invention will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it will be necessary to use an absorption-enhancing agent in combination with a given chimeric protein of the invention. A wide variety of absorption-enhancing agents have been investigated and/or applied in combination with protein drugs for oral delivery and for delivery by other routes (Verhoef, 1990, supra; van Hoogdalem, Pharmac. Ther. 44, 407-443, 1989; Davis, J. Pharm. Pharmacol. 44(Suppl. 1), 186-190, 1992). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides, and diglycerides, (e) non-surfactants, such as unsaturated cyclic ureas, (f) saponins, (g) cyclodextrins, and (h) phospholipids.

Other approaches to enhancing oral delivery of protein drugs, such as the chimeric protein of the present invention, can include the aforementioned chemical modifications to enhance stability to gastrointestinal enzymes and/or increased lipophilicity. Alternatively, the protein drug can be administered in combination with other drugs or substances which directly inhibit proteases and/or other potential sources of enzymatic degradation of proteins. Yet another alternative approach to prevent or delay gastrointestinal absorption of protein drugs, such as the chimeric proteins of the invention, is to incorporate them into a delivery system that is designed to protect the protein from contact with the proteolytic enzymes in the intestinal lumen and to release the intact protein only upon reaching an area favorable for its absorption. A more specific example of this strategy is the use of biodegradable microcapsules or microspheres, both to protect vulnerable drugs from degradation, as well as to effect a prolonged release of active drug (Deasy, in Microencapsulation and Related Processes, Swarbrick, ed., Marcell Dekker, Inc.: New York, 1984, pp. 1-60, 88-89, 208-211). Microcapsules also can provide a useful way to effect a prolonged delivery of a protein drug, such as a cyanovirin or conjugate thereof, after injection (Maulding, J. Controlled Release 6, 167-176, 1987).

Given the aforementioned potential complexities of successful oral delivery of a protein drug, it is preferred in many situations that the chimeric protein of the invention be delivered by one of the numerous other potential routes of delivery of a protein drug. These routes include intravenous, intraarterial, intrathecal, intracisternal, buccal, rectal, nasal, pulmonary, transdermal, vaginal, ocular, and the like (Eppstein, 1988, supra; Siddiqui et al., 1987, supra; Banga et al., 1988, supra; Sanders, 1990, supra; Verhoef, 1990, supra; Barry, in Delivery Systems for Peptide Drugs, Davis et al., eds., Plenum Press: New York, 1986, pp. 265-275; Patton et al., Adv. Drug Delivery Rev. 8, 179-196, 1992). With any of these routes, or, indeed, with any other route of administration or application, a protein drug, such as a cyanovirin or conjugate thereof, may initiate an immunogenic reaction. In such situations it may be necessary to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al., 1981, supra; Abuchowski et al., J. Biol. Chem. 252, 3578-3581, 1977; Lisi et al., J. Appl. Biochem. 4, 19-33, 1982; Wileman et al., J. Pharm. Pharmacol. 38, 264-271, 1986). Such modifications also can have advantageous effects on stability and half-life both in vivo and ex vivo. Other strategies to avoid untoward immune reactions also can include the induction of tolerance by administration initially of only low doses. In any event, it will be apparent from the present disclosure to one skilled in the art that for any particular desired medical application or use of chimeric protein of the invention, the skilled artisan can select from any of a wide variety of possible compositions, routes of administration, or sites of application, whatever is advantageous.

Accordingly, the chimeric protein of the present invention can be formulated into various compositions for use either in therapeutic treatment methods for virally, e.g., HIV, infected individuals, or in prophylactic methods against viral, e.g., HIV, infection of uninfected individuals.

Thus, the present invention provides a composition comprising the present inventive cyanovirin or cyanovirin conjugate, especially a pharmaceutical composition comprising an antiviral effective amount of an isolated and purified cyanovirin or cyanovirin conjugate and a pharmaceutically acceptable carrier. Instead of, or in addition to, the aforementioned isolated and purified chimeric protein of the invention, the composition can comprise viable host cells transformed to directly express a cyanovirin or conjugate thereof in vivo. The composition further can comprise an antiviral effective amount of at least one additional antiviral compound other than the chimeric protein of the invention. Suitable antiviral compounds include AZT, ddI, ddC, gancyclovir, fluorinated dideoxynucleosides, nevirapine, R82913, Ro 31-8959, BI-RJ-70, acyclovir, .alpha.-interferon, recombinant sCD4, michellamines, calanolides, nonoxynol-9, gossypol and derivatives thereof, and gramicidin. The chimeric protein of the invention used in the pharmaceutical composition can be isolated and purified from naturally occurring organisms or from genetically engineered organisms. Similarly, cyanovirin conjugates can be derived from genetically engineered organisms or from chemical coupling.

The present inventive compositions can be used to treat a virally infected animal, such as a human. The compositions of the present invention are particularly useful for inhibiting the growth or replication of a virus, such as a retrovirus, in particular a human immunodeficiency virus, specifically HIV-1 and HIV-2. The compositions are useful in the therapeutic or prophylactic treatment of animals, such as humans, who are infected with a virus or who are at risk for viral infection, respectively. The compositions also can be used to treat objects or materials, such as medical equipment, supplies, or fluids, including biological fluids, such as blood, blood products, and tissues, to prevent viral infection of an animal, such as a human. Such compositions also are useful to prevent sexual transmission of viral infections, e.g., HIV, which is the primary way in which the world's AIDS cases are contracted (Merson, 1993, supra).

Potential virucides used or being considered for application against sexual transmission of HIV are very limited; present agents in this category include, for example, nonoxynol-9 (Bird, AIDS 5, 791-796, 1991), gossypol and derivatives (Polsky et al., Contraception 39, 579-587, 1989; Lin, Antimicrob. Agents Chemother. 33, 2149-2151, 1989; Royer, Pharmacol. Res. 24, 407-412, 1991), and gramicidin (Bourinbair, Life Sci./Pharmacol. Lett. 54, PL5-9, 1994; Bourinbair et al., Contraception 49, 131-137, 1994).

One skilled in the art will appreciate that various routes of administering a drug are available, and, although more than one route may be used to administer a particular drug, a particular route may provide a more immediate and more effective response than by another route. Furthermore, one skilled in the art will appreciate that the particular pharmaceutical carrier employed will depend, in part, upon the particular cyanovirin, conjugate thereof, or host cell employed, and the chosen route of administration. Accordingly, there is a wide variety of suitable formulations of the composition of the present invention.

Formulations suitable for oral, rectal, or vaginal administration can consist of, for example, (a) liquid solutions or suspensions, such as an effective amount of the pure compound(s), and/or host cell(s) engineered to produce the a chimeric protein of the invention, dissolved or suspended in diluents, such as water, culture medium, or saline, (b) capsules, suppositories, sachets, tablets, lozenges, or pastilles, each containing a predetermined amount of the active ingredient(s), as solids, granules, or freeze-dried cells, and (c) oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenges can comprise the active ingredient in a flavor, for example sucrose and acacia or tragacanth, while pastilles can comprise the active ingredient in an inert base, such as gelatin and glycerin, or sucrose and acacia. Suitable formulations for oral or rectal delivery also can be incorporated into synthetic and natural polymeric microspheres, or other means to protect the agents of the present invention from degradation within the gastrointestinal tract (see, for example, Wallace et al., Science 260, 912-915, 1993). Formulations for rectal or vaginal administration can be presented as a suppository with a suitable aqueous or nonaqueous base; the latter can comprise, for example, cocoa butter or a salicylate. Furthermore, formulations suitable for vaginal administration can be presented as pessaries, suppositories, tampons, creams, gels, pastes, foams, or spray formulas containing, in addition to the active ingredient, such as, for example, freeze-dried lactobacilli genetically engineered to directly produce a chimeric protein of the present invention, such carriers as are known in the art to be appropriate. Similarly, the active ingredient can be combined with a lubricant as a coating on a condom.

For in vivo uses, the dose of a chimeric protein of the invention, host cells producing a chimeric protein of the invention, or composition thereof, administered to an animal, particularly a human, in the context of the present invention should be sufficient to effect a prophylactic and/or therapeutic response in the individual over a reasonable time-frame. The dose used to achieve a desired virucidal concentration in vivo (e.g., 0.1-1000 nM) will be determined by the potency of the particular chimeric protein of the invention, the severity of the disease state of infected individuals, as well as, in the case of systemic administration, the body weight and age of the infected individual. The effective or virucidal dose also will be determined by the existence of any adverse side-effects that may accompany the administration of the particular chimeric protein of the invention employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a chimeric protein of the invention, alone or in combination with other antiviral agents, calculated in a quantity sufficient to produce the desired effect in association with a pharmaceutically acceptable carrier, diluent, or vehicle.

The specifications for the unit dosage forms of the present invention depend on the particular chimeric protein of the invention employed, and the effect to be achieved, as well as the pharmacodynamics associated with each chimeric protein of the invention, host cells, or composition thereof in the treated animal. The dose administered should be an "anitiviral effective amount" or "virucidal effective amount" or an amount necessary to achieve an "effective virucidal level" in the individual animal, e.g., the human patient.

Since the "effective virucidal level" is used as the preferred endpoint for dosing, the actual dose and schedule can vary, depending upon interindividual differences in pharmacokinetics, drug distribution, and metabolism. The "effective virucidal level" can be defined, for example, as the blood or tissue level (e.g., 0.1-1000 nM) desired in the patient that corresponds to a concentration of one or more chimeric protein of the invention, which inhibits a virus, such as HIV-1 and/or HIV-2, in an assay known to predict for clinical antiviral activity of chemical compounds and biological agents. The "effective virucidal level" for agents of the present invention also can vary when the chimeric protein of the invention, is used in combination with AZT or other known antiviral compounds or combinations thereof.

One skilled in the art can easily determine the appropriate dose, schedule, and method of administration for the exact formulation of the composition being used, in order to achieve the desired "effective virucidal level" in the individual patient. One skilled in the art also can readily determine and use an appropriate indicator of the "effector concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it may be desirable to utilize a "mega-dosing" regimen, wherein a large dose of a selected chimeric protein of the invention is administered, and time thereafter is allowed for the drug to act, and then a suitable reagent is administered to the individual to inactivate the drug.

The pharmaceutical composition can contain other pharmaceuticals, in conjunction with the chimeric protein of the invention, or host cells producing the chimeric protein of the invention, when used to therapeutically treat a viral infection, such as that which causes AIDS. Representative examples of these additional pharmaceuticals include antiviral compounds, virucides, immunomodulators, immunostimulants, antibiotics, and absorption enhancers. Exemplary antiviral compounds include AZT, ddI, ddC, gancylclovir, fluorinated dideoxynucleosides, nonnucleoside analog compounds, such as nevirapine (Shih et al., PNAS 88, 9878-9882, 1991), TIBO derivatives, such as R82913 (White et al., Antiviral Res. 16, 257-266, 1991), BI-RJ-70 (Merigan, Am. J. Med. 90 (Suppl.4A), 8S-17S, 1991), michellamines (Boyd et al., J. Med. Chem. 37, 1740-1745, 1994), and calanolides (Kashman et al., J. Med. Chem. 35, 2735-2743, 1992), nonoxynol-9, gossypol and derivatives, and gramicidin (Bourinbair et al., 1994, supra). Exemplary immunomodulators and immunostimulants include various interleukins, sCD4, cytokines, antibody preparations, blood transfusions, and cell transfusions. Exemplary antibiotics include antifungal agents, antibacterial agents, and anti-Pneumocystitis carnii agents. Exemplary absorption enhancers include bile salts and other surfactants, saponins, cyclodextrins, and phospholipids.

In a preferred embodiment of the present invention, a method of female-controllable prophylaxis against HIV infection comprises the intravaginal administration and/or establishment of, in a female human, a persistent intravaginal population of lactobacilli that have been transformed with a coding sequence of the chimeric protein of the present invention to produce, over a prolonged time, effective virucidal levels of a cyanovirin or conjugate thereof, directly on or within the vaginal and/or cervical and/or uterine mucosa.

In another aspect, the invention is a vector comprising the chimeric protein of the invention. In another aspect, the invention is a host cell containing the vector comprising the chimeric protein of the invention.

It also will be appreciated by one skilled in the art that a DNA sequence of the chimeric protein of the invention can be inserted ex vivo into mammalian cells previously removed from a given animal, in particular a human. Such transformed autologous or homologous host cells, reintroduced into the animal or human, will express directly the corresponding chimeric protein of the invention in vivo. The feasibility of such a therapeutic strategy to deliver a therapeutic amount of an agent in close proximity to the desired target cells and pathogens (e.g., to the virus, more particularly to the retrovirus, specifically to HIV and its envelope glycoprotein gp120), has been demonstrated in studies with cells engineered ex vivo to express sCD4 (Morgan et al., 1994, supra). As an alternative to ex vivo insertion of the DNA sequences of the present invention, such sequences can be inserted into cells directly in vivo, such as by use of an appropriate viral or other suitable vector. Such cells transfected in vivo may be expected to produce antiviral amounts of the chimeric protein directly in vivo.

Given the present disclosure, it will be additionally appreciated that a DNA sequence corresponding to a chimeric protein of the invention can be inserted into suitable nonmammalian host cells, and that such host cells will express therapeutic or prophylactic amounts of the chimeric protein directly in vivo within a desired body compartment of an animal, in particular a human.

In another aspect, the invention is a method of producing a protein, which method comprises expressing a protein in a host cell. In certain embodiments, the host cell is an autologous or a homologous mammalian cell. In certain embodiments, the host cell is a nonpathogenic bacterium or a nonpathogenic yeast. In certain embodiments, the host cell is a *lactobacillus*.

The present invention also provides antibodies directed to the chimeric protein of the invention. The availability of antibodies to any given protein is highly advantageous, as it provides the basis for a wide variety of qualitative and quantitative analytical methods, separation and purification methods, and other useful applications directed to the subject proteins. Accordingly, given the present disclosure and the proteins of the present invention, it will be readily apparent to one skilled in the art that antibodies, in particular antibodies specifically binding to a protein of the present invention, can be prepared using well-established methodologies (e.g., such as the methodologies described in detail by Harlow and Lane, in Antibodies. A Laboratory Manual, Cold Spring Harbor Laboratory, Cold Spring Harbor, 1988, pp. 1-725). Such antibodies can comprise both polyclonal and monoclonal antibodies. Furthermore, such antibodies can be obtained and employed either in solution-phase or coupled to a desired solid-phase matrix. Having in hand such antibodies as provided by the present invention, one skilled in the art will further appreciate that such antibodies, in conjunction with well-established procedures (e.g., such as described by Harlow and Lane (1988, supra) comprise useful methods for the detection, quantification, or purification of a chimeric protein of the invention, or host cell transformed to produce a chimeric protein of the invention.

The invention will be illustrated in more detail with reference to the following Examples, but it should be understood that the present invention is not deemed to be limited thereto.

EXAMPLES

Example 1

Materials and Methods
Reagents and Proteins

The following reagents were obtained from the NIH AIDS Reference and Reagent Program, Division of AIDS, NIAID: HIV-1$_{BaL}$ gp120, HIV-1$_{SF162}$ gp120, HIV-1$_{CM235}$ gp120 from Protein Sciences, Corporation, HIV-1 gp120 Monoclonal Antibody (2G12) from Dr. Hermann Katinger; HIV-1 gp120 Monoclonal Antibody (F105) from Dr. Marshall Posner and Dr. Lisa Cavacini. HIV-193$_{MW959}$ gp120, HIV-1$_{92UG21-9}$ gp120, HIV-1$_{92US715}$ gp120 and SIV$_{PBj2-8}$ HIV-1 gp120 and AN1 were provided by colleagues. Monoclonal Antibody 17b was obtained from Strategic Biosolutions. CVN plasmid and anti-CVN polyclonal antibodies were a gift from Biosyn Inc.

Example 2

Expression and Purification of CVN and CVN-12p1

BL21 Codon Plus (DE3) RIL competent cells (Stratagene) containing either CVN or the chimera were grown in Superbroth supplemented with 1 mM MgSO$_4$, 0.5% glucose and 25 μg/ml kanamycin in a 37° C. shaking incubator until the absorbance at 600 nm read 1.2. Protein expression was induced with 1 mM IPTG for two hours at 37° C. The cells were then centrifuged at 3,000 rpm for 15 minutes and the resulting pellet was resuspended in 100 mM Tris, 1 mM EDTA and 20% sucrose. This was mixed for one hour at 4° C. followed by resuspension in cold water which was stirred overnight at 4° C. The lysates were centrifuged at 10,000 rpm for thirty minutes and the supernatant sterile filtered and dialyzed into 50 mM NaH$_2$PO$_4$, 300 mM NaCl and 10 mM imidazole pH 8.0. The extracts were then adsorbed onto NiNTA agarose beads (Qiagen) and washed with three column volumes of 50 mM NaH$_2$PO$_4$, 300 mM NaCl and 20 mM imidazole pH 8.0. The protein was eluted with 50 mM NaH$_2$PO$_4$, 300 mM NaCl and 250 mM imidazole pH 8.0.

SDS-polyacrylamide gel electrophoresis (SDS-PAGE) was performed on a 4-20% polyacrylamide gel under reducing conditions (1% β-mercaptoethanol). Proteins were detected with Simply Blue Coomassie Stain (Invitrogen). For immunoblot assays, proteins were transferred to nitrocellulose. The proteins were detected with a 1:10,000 dilution of polyclonal rabbit anti-CVN followed by anti-rabbit HRP. Images were detected with chemilluminescent substrate (Amersham) and exposed to film. Proteins were quantified based on their absorbance at 280 nm.

Example 3

YU2 gp120 and sCD4 Production

Recombinant YU2-gp120 from HIV-1 was produced in Schneider 2 (S2) *Drosophila* cells under the control of the metallothionein promoter as previously described[41]. In brief, the cells were grown in Insect-Xpress medium (Cambrex) supplemented with 10 mM L-glutamine and 1% antibiotic/antimycotic in shaker flasks at 28° C. Protein expression was induced with 750 μM copper sulfate until the viability as determined by trypan blue was 70%. The supernatant was fractionated on an F105 mAb affinity column, washed extensively and eluted with 100 mM glycine-HCl, pH 2.1. The samples were neutralized with 1M Tris, pH 8.0 buffer immediately after elution. Fractions containing gp120 were pooled and dialyzed overnight at 4° C. against Dulbecco's phosphate buffered saline.

CHO-ST4.2 cells, which secrete the full extracellular domain of CD4, were obtained from Dr. Dan Littman through the AIDS Research and Reference program Division of AIDS, NIAID. They were grown in a hollow fiber bioreactor (FiberCell Systems, Inc.) in HiQ CDM4CHO media (Hyclone) supplemented with 400 mM L-glutamine, 300 nM methotrexate and 1% antibiotic/antimycotic. Supernatant from the CHO cells was diluted 10-fold in cold 50 mM MES/50 mM NaCl pH 6.0 and passed through a 0.2 μM sterile filter. They were equilibrated with 50 mM MES/50 mM NaCl pH 6.0 at 4° C., and fractions collected from a 50 mM MES/500 mM NaCl pH 6.0 gradient. Fractions were dialyzed into 50 mM bis-tris propane pH 6.0, adjusted to pH 9.0 and loaded onto a Q-column equilibrated with bis-tris propane pH 9.0. The column flow through containing purified sCD4 was pooled and dialyzed into DPBS overnight at 4° C. All proteins were analyzed by SDS-PAGE/Coomassie stain to be of greater than 95% purity.

Example 4

Biacore Assays

All surface plasmon resonance studies were performed on a Biacore 3000 (Biacore Inc., Uppsala, Sweden). CM5 dextran chip was derivatized by amine coupling with 250 RUs of YU2 gp120 or 2B6R (anti-IL5 receptor βchain) IgG as a control surface. Either CVN alone or the chimera was passed over the surface at a flow rate of 30 μL/min, for two minutes followed by a four minute dissociation period. Surfaces were regenerated with multiple short pulses of 10 mM glycine HCl, pH 1.7.

Example 5

ELISA Assays

Ninety-six well plates (Corning) were coated with either 100 ng of the indicated gp120 or BSA overnight at 4° C. The wells were washed three times with 1×PBS-T (PBS, 0.1% Tween) and non-specific binding blocked with 1% (wt/vol) BSA in PBS. This was followed by three washes with PBST and incubation with the indicated doses of either CVN or the chimera for one hour at room temperature. The wells were washed and incubated with a 1/1000 dilution of rabbit anti-CVN polyclonal antibody. After a one hour incubation, the wells were washed and incubated with a 1/2500 dilution of anti-rabbit HRP (Amersham) for one hour at room temperature. The wells were washed three times and the extent of binding was then determined by OPD (o-phenylenediamine, Sigma) and absorbance measured at 450 nm.

Experiments were in triplicate and corrected for non-specific binding to a BSA surface.

Example 6

Antibody inhibition assays were performed as described above but with either 1:20,000 dilution of F105, 50 μg/ml dilution of 2G12 or 2 μg/ml 17b added to the CVN or chimera dilutions. The extent of CVN binding was detected with rabbit anti-CVN primary antibody. The data was plotted as percent of binding in the absence of either CVN or the chimera.

For CD4 competition assays, 2 ng/μl YU2-gp120 or BSA was adsorbed onto a 96 well plate. Serial dilutions of either CVN or the chimera were added for thirty minutes followed by the addition of 0.5 μg/ml sCD4 for thirty minutes. The wells were washed and then incubated with anti-CD4 (ARP356-NIBSC UK) for one hour at room temperature. This was followed by washing and addition of anti-mouse HRP conjugated secondary antibody. The extent of binding was then determined by o-phenylenediamine (OPD) (Sigma) as described above.

Example 7

Viral Synergy Studies

Doubling dilutions of each drug (12p1 or CVN), alone or in fixed combinations, were incubated with HIV-1 BaL (R5) for 1 h in 100 μl volume prior to the addition of PM-1 cells (100 μl at 0.50×10$^6$ cells/ml). Dilutions and cells were in RPMI supplemented with 10% fetal calf serum, pen, strep and glutamine. Cells were incubated for 7 days and viral replication determined by gp120 ELISA. Each condition was performed in sextuplet and the mean used to calculate IC$_{50}$ values. Analysis of combined effects was also carried out using the median effect principle developed by Chou and Talalay[39,40], and using the computer program CalcuSyn (BioSoft).

While the invention has been described in detail and with reference to specific examples thereof, it will be apparent to one skilled in the art that various changes and modifications can be made therein without departing from the spirit and scope thereof.

REFERENCES

1. Shattock R J, Moore J P. Inhibiting sexual transmission of HIV-1 infection. Nat Rev Microbiol 2003; 1(1):25-34.
2. Miller C J, Shattock R J. Target cells in vaginal HIV transmission. Microbes Infect 2003; 5(1):59-67.
3. Pope M, Haase A T. Transmission, acute HIV-1 infection and the quest for strategies to prevent infection. Nat Med 2003; 9(7):847-852.
4. Shattock R, Solomon S. Microbicides—aids to safer sex. Lancet 2004; 363(9414): 1002-1003.
5. Allan J S, Coligan J E, Barin F, McLane M F, Sodroski J G, Rosen C A, Haseltine W A, Lee T H, Essex M. Major glycoprotein antigens that induce antibodies in AIDS patients are encoded by HTLV-III. Science 1985; 228(4703):1091-1094.
6. Earl P L, Moss B, Doms R W. Folding, interaction with GRP78-BiP, assembly, and transport of the human immunodeficiency virus type 1 envelope protein. J Virol 1991; 65(4): 2047-2055.
7. Robey W G, Safai B, Oroszlan S, Arthur L O, Gonda M A, Gallo R C, Fischinger P J. Characterization of envelope and core structural gene products of HTLV-III with sera from AIDS patients. Science 1985; 228(4699):593-595.
8. Sattentau Q J, Moore J P, Vignaux F, Traincard F, Poignard P. Conformational changes induced in the envelope glycoproteins of the human and simian immunodeficiency viruses by soluble receptor binding. J Virol 1993; 67(12): 7383-7393.
9. Sattentau Q J, Zolla-Pazner S, Poignard P. Epitope exposure on functional, oligomeric HIV-1 gp41 molecules. Virology 1995; 206(1):713-717.
10. Alkhatib G, Combadiere C, Broder C C, Feng Y, Kennedy P E, Murphy P M, Berger E A. CC CKR5: a RANTES, MIP-alpha, MIP-1beta receptor as a fusion cofactor for macrophage-tropic HIV-1. Science 1996; 272(5270): 1955-1958.
11. Choe H, Farzan M, Sun Y, Sullivan N, Rollins B, Ponath P D, Wu L, Mackay C R, LaRosa G, Newman W, Gerard N, Gerard C, Sodroski J. The beta-chemokine receptors CCR3 and CCR5 facilitate infection by primary HIV-1 isolates. Cell 1996; 85(7):1135-1148.
12. Deng H, Liu R, Ellmeier W, Choe S, Unutmaz D, Burkhart M, Di Marzio P, Marmon S, Sutton R E, Hill C M, Davis C B, Peiper S C, Schall T J, Littman D R, Landau N R. Identification of a major co-receptor for primary isolates of HIV-1. Nature 1996; 381(6584):661-666.
13. Feng Y, Broder C C, Kennedy P E, Berger E A. HIV-1 entry cofactor: functional cDNA cloning of a seven-transmembrane, G protein-coupled receptor. Science 1996; 272 (5263):872-877.
14. Boyd M R, Gustafson K R, McMahon J B, Shoemaker R H, O'Keefe B R, Mori T, Gulakowski R J, Wu L, Rivera M I, Laurencot C M, Currens M J, Cardellina J H, 2nd, Buckheit R W, Jr., Nara P L, Pannell L K, Sowder R C, 2nd, Henderson L E. Discovery of cyanovirin-N, a novel human immunodeficiency virus-inactivating protein that binds viral surface envelope glycoprotein gp120: potential applications to microbicide development. Antimicrob Agents Chemother 1997; 41(7):1521-1530.

15. Tsai C C, Emau P, Jiang Y, Agy M B, Shattock R J, Schmidt A, Morton W R, Gustafson K R, Boyd M R. Cyanovirin-N inhibits AIDS virus infections in vaginal transmission models. AIDS Res Hum Retroviruses 2004; 20(1): 11-18.

16. Tsai C C, Emau P, Jiang Y, Tian B, Morton W R, Gustafson K R, Boyd M R. Cyanovirin-N gel as a topical microbicide prevents rectal transmission of SHIV89.6P in macaques. AIDS Res Hum Retroviruses 2003; 19(7):535-541.

17. O'Keefe B R, Shenoy S R, Xie D, Zhang W, Muschik J M, Currens M J, Chaiken I, Boyd M R. Analysis of the interaction between the HIV-inactivating protein cyanovirin-N and soluble forms of the envelope glycoproteins gp 120 and gp41. Mol Pharmacol 2000; 58(5):982-992.

18. Bolmstedt A J, O'Keefe B R, Shenoy S R, McMahon J B, Boyd M R. Cyanovirin-N defines a new class of antiviral agent targeting N-linked, high-mannose glycans in an oligosaccharide-specific manner. Mol Pharmacol 2001; 59(5): 949-954.

19. Mori T, Gustafson K R, Pannell L K, Shoemaker R H, Wu L, McMahon J B, Boyd M R. Recombinant production of cyanovirin-N, a potent human immunodeficiency virus-inactivating protein derived from a cultured cyanobacterium. Protein Expr Purif 1998; 12(2):151-158.

20. Shenoy S R, O'Keefe B R, Bolmstedt A J, Cartner L K, Boyd M R. Selective interactions of the human immunodeficiency virus-inactivating protein cyanovirin-N with high-mannose oligosaccharides on gp120 and other glycoproteins. J Pharmacol Exp Ther 2001; 297(2):704-710.

21. Bewley C A. Solution structure of a cyanovirin-N:Man alpha 1-2Man alpha complex: structural basis for high-affinity carbohydrate-mediated binding to gp120. Structure 2001; 9(10):931-940.

22. Bewley C A, Otero-Quintero S. The potent anti-HIV protein cyanovirin-N contains two novel carbohydrate binding sites that selectively bind to Man(8) D1D3 and Man(9) with nanomolar affinity: implications for binding to the HIV envelope protein gp120. J Am Chem Soc 2001; 123(17): 3892-3902.

23. Botos I, O'Keefe B R, Shenoy S R, Cartner L K, Ratner D M, Seeberger P H, Boyd M R, Wlodawer A. Structures of the complexes of a potent anti-HIV protein cyanovirin-N and high mannose oligosaccharides. J Biol Chem 2002; 277(37): 34336-34342.

24. Sandstrom C, Berteau O, Gemma E, Oscarson S, Kenne L, Gronenborn A M. Atomic mapping of the interactions between the antiviral agent cyanovirin-N and oligomannosides by saturation-transfer difference NMR. Biochemistry 2004; 43(44): 13926-13931.

25. Witvrouw M, Fikkert V, Hantson A, Pannecouque C, O'Keefe B R, McMahon J, Stamatatos L, de Clercq E, Bolmstedt A. Resistance of human immunodeficiency virus type 1 to the high-mannose binding agents cyanovirin N and concanavalin A. J Virol 2005; 79(12):7777-7784.

26. Barrientos L G, Louis J M, Botos I, Mori T, Han Z, O'Keefe B R, Boyd M R, Wlodawer A, Gronenborn A M. The domain-swapped dimer of cyanovirin-N is in a metastable folded state: reconciliation of X-ray and NMR structures. Structure 2002; 10(5):673-686.

27. Yang F, Bewley C A, Louis J M, Gustafson K R, Boyd M R, Gronenborn A M, Clore G M, Wlodawer A. Crystal structure of cyanovirin-N, a potent HIV-inactivating protein, shows unexpected domain swapping. J Mol Biol 1999; 288 (3):403-412.

28. Bewley C A, Gustafson K R, Boyd M R, Covell D G, Bax A, Clore G M, Gronenborn A M. Solution structure of cyanovirin-N, a potent HIV-inactivating protein. Nat Struct Biol 1998; 5(7):571-578.

29. Clore G M, Bewley C A. Using conjoined rigid body/torsion angle simulated annealing to determine the relative orientation of covalently linked protein domains from dipolar couplings. J Magn Reson 2002; 154(2):329-335.

30. Chang L C, Bewley C A. Potent inhibition of HIV-1 fusion by cyanovirin-N requires only a single high affinity carbohydrate binding site: characterization of low affinity carbohydrate binding site knockout mutants. J Mol Biol 2002; 318(1):1-8.

31. Ferrer M, Harrison S C. Peptide ligands to human immunodeficiency virus type 1 gp120 identified from phage display libraries. J Virol 1999; 73(7):5795-5802.

32. Biorn A C, Cocklin S, Madani N, Si Z, Ivanovic T, Samanen J, Van Ryk D I, Pantophlet R, Burton D R, Freire E, Sodroski J, Chaiken I M. Mode of action for linear peptide inhibitors of HIV-1 gp120 interactions. Biochemistry 2004; 43(7):1928-1938.

33. Chou T C. The Median-Effect Principle and the Combination Index for Quantitation of Synergism and Antagonism. In: Rideout D C, editor. Synergism and Antagonism in Chemotherapy. San Diego: San Diego Academic Press; 1991. p 61.

34. Chou T C, Talalay P. Applications of the median effect principle for the assessment of low dose risk of carcinogens and for the quantitation of synergism and antagonism of chemotherapeutic agents. In: Harrap K R, Conners T A, editors. New avenues in developmental cancer chemotherap. New York: Academic Press; 1987. p 37-63.

35. Culp J S, Johansen H, Hellmig B, Beck J, Matthews T J, Delers A, Rosenberg M. Regulated expression allows high level production and secretion of HIV-1 gp120 envelope glycoprotein in *Drosophila* Schneider cells. Biotechnology (N Y) 1991; 9(2):173-177.

36. Huston J S, Levinson D, Mudgett-Hunter M, Tai M S, Novotny J, Margolies M N, Ridge R J, Bruccoleri R E, Haber E, Crea R, et al. Protein engineering of antibody binding sites: recovery of specific activity in an anti-digoxin single-chain Fv analogue produced in *Escherichia coli*. Proc Natl Acad Sci USA 1988; 85(16):5879-5883.

37. Colleluori D M, Tien D, Kang F, Pagliei T, Kuss R, McCormick T, Watson K, McFadden K, Chaiken I, Buckheit R W, Jr., Romano J W. Expression, purification, and characterization of recombinant cyanovirin-N for vaginal anti-HIV microbicide development. Protein Expr Purif 2005; 39(2): 229-236.

38. Dey B, Lerner D L, Lusso P, Boyd M R, Elder J H, Berger E A. Multiple antiviral activities of cyanovirin-N: blocking of human immunodeficiency virus type 1 gp120 interaction with CD4 and coreceptor and inhibition of diverse enveloped viruses. J Virol 2000; 74(10):4562-4569.

39. Doria-Rose N A, Learn G H, Rodrigo A G, Nickle D C, Li F, Mahalanabis M, Hensel M T, McLaughlin S, Edmonson P F, Montefiori D, Barnett S W, Haigwood N L, Mullins J I. Human immunodeficiency virus type 1 subtype B ancestral envelope protein is functional and elicits neutralizing antibodies in rabbits similar to those elicited by a circulating subtype B envelope. J Virol 2005; 79(17): 11214-11224.

40. Esser M T, Mori T, Mondor I, Sattentau Q J, Dey B, Berger E A, Boyd M R, Lifson J D. Cyanovirin-N binds to gp120 to interfere with CD4-dependent human immunodeficiency virus type I virion binding, fusion, and infectivity but does not affect the CD4 binding site on gp120 or soluble CD4-induced conformational changes in gp120. J Virol 1999; 73(5):4360-4371.

41. Mori T, Boyd M R. Cyanovirin-N, a potent human immunodeficiency virus-inactivating protein, blocks both CD4-dependent and CD4-independent binding of soluble gp120 (sgp120) to target cells, inhibits sCD4-induced binding of sgp120 to cell-associated CXCR4, and dissociates bound sgp120 from target cells. Antimicrob Agents Chemother 2001; 45(3):664-672.

42. Thali M, Moore J P, Furman C, Charles M, Ho D D, Robinson J, Sodroski J. Characterization of conserved human immunodeficiency virus type 1 gp120 neutralization epitopes exposed upon gp120-CD4 binding. J Virol 1993; 67(7):3978-3988.

43. Zhang W, Canziani G, Plugariu C, Wyatt R, Sodroski J, Sweet R, Kwong P, Hendrickson W, Chaiken I. Conformational changes of gp120 in epitopes near the CCR5 binding site are induced by CD4 and a CD4 miniprotein mimetic. Biochemistry 1999; 38(29):9405-9416.

44. Posner M R, Cavacini L A, Emes C L, Power J, Byrn R. Neutralization of HIV-1 by F105, a human monoclonal antibody to the CD4 binding site of gp120. J Acquir Immune Defic Syndr 1993; 6(1):7-14.

45. Posner M R, Elboim H S, Cannon T, Cavacini L, Hideshima T. Functional activity of an HIV-1 neutralizing IgG human monoclonal antibody: ADCC and complement-mediated lysis. AIDS Res Hum Retroviruses 1992; 8(5):553-558.

46. Thali M, Olshevsky U, Furman C, Gabuzda D, Posner M, Sodroski J. Characterization of a discontinuous human immunodeficiency virus type I gp120 epitope recognized by a broadly reactive neutralizing human monoclonal antibody. J Virol 1991; 65(11):6188-6193.

47. Xiang S H, Kwong P D, Gupta R, Rizzuto C D, Casper D J, Wyatt R, Wang L, Hendrickson W A, Doyle M L, Sodroski J. Mutagenic stabilization and/or disruption of a CD4-bound state reveals distinct conformations of the human immunodeficiency virus type 1 gp120 envelope glycoprotein. J Virol 2002; 76(19):9888-9899.

48. Gustafson K R, Sowder R C, 2nd, Henderson L E, Cardellina J H, 2nd, McMahon J B, Rajamani U, Pannell L K, Boyd M R. Isolation, primary sequence determination, and disulfide bond structure of cyanovirin-N, an anti-HIV (human immunodeficiency virus) protein from the cyanobacterium *Nostoc ellipsosporum*. Biochem Biophys Res Commun 1997; 238(1):223-228.

49. Newton D L, Xue Y, Olson K A, Fett J W, Rybak S M. Angiogenin single-chain immunofusions: influence of peptide linkers and spacers between fusion protein domains. Biochemistry 1996; 35(2):545-553.

50. Robinson C R, Sauer R T. Optimizing the stability of single-chain proteins by linker length and composition mutagenesis. Proc Natl Acad Sci USA 1998; 95(11):5929-5934.

51. Arai R, Ueda H, Kitayama A, Kamiya N, Nagamune T. Design of the linkers which effectively separate domains of a bifunctional fusion protein. Protein Eng 2001; 14(8):529-532.

52. Biorn A. C. Cocklin S. et al, (2004) Biochemistry 7:5795-5802.

53. Gallo S. A. et al (2003) Biochem and Biophys Acta 1614:36-50.

54. Kwong P. et al (1998) Nature 393:648-59.

55. Moore J. P. and Doms J. P (2003) PNAS 100: 10598-10602.

What is claimed is:

1. A chimeric protein comprising a first amino acid sequence of cyanovirin, a second amino acid sequence of 12p1 and a linker covalently connecting the first amino acid sequence with the second amino acid sequence, wherein the first amino acid sequence is selected from the group consisting of SEQ ID NO: 2 and SEQ ID NO: 4, and the second amino acid sequence is selected from the group consisting of SEQ ID NO: 12 and SEQ ID NO: 13, and wherein the linker has one through seven penta-peptide repeats of glycine and serine.

2. The chimeric protein of claim 1, wherein the linker comprises a sequence encoded by SEQ ID NO: 8.

3. The chimeric protein of claim 2, wherein the linker has at least three repeats of the sequence encoded by SEQ ID NO: 8.

4. The chimeric protein of claim 2, wherein the linker has at least five repeats of the sequence encoded by SEQ ID NO:8.

5. The chimeric protein of claim 1 encoded by SEQ ID NO: 10.

6. The chimeric protein of claim 1 encoded by SEQ ID NO: 15.

7. The chimeric protein of claim 3, wherein the linker is a sequence encoded by SEQ ID NO: 9.

8. A pharmaceutical composition comprising the chimeric protein of claim 1 and a pharmaceutically acceptable carrier.

9. A pharmaceutical composition comprising:

(i) an isolated and purified protein of cyanovirin having an amino acid sequence selected from the group consisting of SEQ ID NO: 2 and SEQ ID NO: 4; and (ii) an isolated and purified peptide having an amino acid sequence selected from the group consisting of SEQ ID NO: 12 and SEQ ID NO: 13.

10. A method of inhibiting HIV in a mammal comprising contacting a cell of the mammal with the pharmaceutical composition of claim 9 in an amount effective to block HIV binding to the cell.

11. A method of inhibiting HIV in a mammal comprising contacting a cell of the mammal with the pharmaceutical composition of claim 8 in an amount effective to block HIV binding to the cell.

* * * * *

UNITED STATES PATENT AND TRADEMARK OFFICE
CERTIFICATE OF CORRECTION

Page 1 of 1

PATENT NO. : 8,093,046 B2
APPLICATION NO. : 11/756567
DATED : January 10, 2012
INVENTOR(S) : Karyn McFadden and Irwin Chaiken It is certified that error appears in the above-identified patent and that said Letters Patent is hereby corrected as shown below:

Col. 1, beginning at line 12 through line 18, please delete the paragraph and replace with the following paragraph:

-- STATEMENT REGARDING FEDERALLY SPONSORED RESEARCH OR DEVELOPMENT

The invention was made with government support under grant numbers P01 GM 56550, PA-01-075 and AI071965 from the National Institutes of Health. The government has certain rights in the invention. --

Signed and Sealed this
Sixteenth Day of October, 2012

David J. Kappos
*Director of the United States Patent and Trademark Office*